United States Patent
Sato et al.

(10) Patent No.: US 11,666,759 B2
(45) Date of Patent: Jun. 6, 2023

(54) NERVE STIMULATING APPARATUS, BIOMETRIC INFORMATION MEASURING SYSTEM, AND METHOD OF SETTING STIMULUS GENERATING TIMINGS OF BIOMETRIC INFORMATION MEASURING SYSTEM

(71) Applicants: Shinji Sato, Tokyo (JP); Sukchan Kim, Tokyo (JP); Taishi Watanabe, Tokyo (JP); Yuki Mitani, Tokyo (JP); Yuki Miyano, Tokyo (JP); Shigenori Kawabata, Tokyo (JP); Toru Sasaki, Tokyo (JP)

(72) Inventors: Shinji Sato, Tokyo (JP); Sukchan Kim, Tokyo (JP); Taishi Watanabe, Tokyo (JP); Yuki Mitani, Tokyo (JP); Yuki Miyano, Tokyo (JP); Shigenori Kawabata, Tokyo (JP); Toru Sasaki, Tokyo (JP)

(73) Assignees: Ricoh Company, Ltd, Tokyo (JP); National University Corporation Tokyo Medical and Dental University, Tokyo (JP)

( * ) Notice: Subject to any disclaimer, the term of this patent is extended or adjusted under 35 U.S.C. 154(b) by 297 days.

(21) Appl. No.: 17/069,193

(22) Filed: Oct. 13, 2020

(65) Prior Publication Data
US 2021/0113837 A1    Apr. 22, 2021

(30) Foreign Application Priority Data
Oct. 16, 2019    (JP) .............................. JP2019-189561

(51) Int. Cl.
*A61N 1/36*    (2006.01)

(52) U.S. Cl.
CPC ..... *A61N 1/36031* (2017.08); *A61N 1/36034* (2017.08)

(58) Field of Classification Search
CPC ............ A61N 1/36031; A61N 1/36034; A61N 1/0456; A61B 5/242; A61B 5/389; A61B 5/407; A61B 5/05
See application file for complete search history.

(56) References Cited

U.S. PATENT DOCUMENTS 10,722,701 B2   7/2020 Ishibe et al.
2014/0243931 A1   8/2014 Parker et al.
(Continued)

FOREIGN PATENT DOCUMENTS

JP        2017-099450      6/2017
JP   WO 2017/094221 A1 *  6/2017   ........... A61B 5/0488
(Continued)

OTHER PUBLICATIONS

Extended European Search Report for 20201614.3 dated Feb. 18, 2021.

*Primary Examiner* — Amanda K Hulbert
*Assistant Examiner* — Philip C Edwards
(74) *Attorney, Agent, or Firm* — IPUSA, PLLC

(57) ABSTRACT

A nerve stimulating apparatus includes a plurality of stimulating units configured to respectively apply stimuli to a plurality of nerve regions branching from a particular nerve region of a living body, and a stimulation timing controller configured to set generating timings of respectively generating the stimuli at the plurality of stimulating units. The stimulation timing controller sets the generating timings of generating the stimuli at the plurality of stimulating units based on response results of the particular nerve region, the response results being obtained in response to the stimuli that are respectively generated at the plurality of stimulating units and that are respectively applied to the plurality of (Continued)

nerve regions, and the response results being measured by a biometric information measuring apparatus that measures biometric information.

14 Claims, 18 Drawing Sheets

(56) References Cited

U.S. PATENT DOCUMENTS

| | | | |
|---|---|---|---|
| 2014/0275926 A1* | 9/2014 | Scott | A61B 5/24 600/377 |
| 2018/0333062 A1 | 11/2018 | Watanabe | |

FOREIGN PATENT DOCUMENTS

| JP | 2017-209322 | 11/2017 |
|---|---|---|
| JP | 2018-126284 | 8/2018 |
| JP | 2018-192236 | 12/2018 |
| JP | 2020-151234 | 9/2020 |

* cited by examiner

NERVE STIMULATING APPARATUS, BIOMETRIC INFORMATION MEASURING SYSTEM, AND METHOD OF SETTING STIMULUS GENERATING TIMINGS OF BIOMETRIC INFORMATION MEASURING SYSTEM

CROSS-REFERENCE TO RELATED APPLICATION

The present application is based on and claims priority under 35 U.S.C. § 119 to Japanese Patent Application No. 2019-189561, filed on Oct. 16, 2019, the contents of which are incorporated herein by reference in their entirety.

BACKGROUND OF THE INVENTION

1. Field of the Invention

The present disclosure relates to a nerve stimulating apparatus, a biometric information measuring system, and a method of setting stimulus generating timings of the biometric information measuring system.

2. Description of the Related Art

A method of determining, for example, a disease by obtaining magnetic fields generated by nerves or the like of a living body from a biomagnetic field measuring system as biometric information, and evaluating, for example, nerve activities of the living body is known. The biomagnetic field measuring system includes, for example, a nerve stimulating apparatus and a biomagnetic field measuring device. The nerve stimulating apparatus provides electrical stimuli to the living body from electrodes attached to a body surface of the living body to induce neural activities. The biomagnetic field measuring device measures magnetic fields generated by nerves in response to the electrical stimuli as magnetic field signals and displays a waveform of the measured magnetic field signals on a display device, for example.

In this kind of the biomagnetic field measuring system, the electrical stimulus is successively applied to the living body from each of multiple electrodes attached to close positions on the body surface, and any one of the electrodes generating a neural activity greater than or equal to a desired value is selected as an electrode that provides the electrical stimulus to the living body (Patent Document 1).

RELATED-ART DOCUMENTS

Patent Documents

Patent Document 1: Japanese Laid-Open Patent Publication No. 2017-99450

SUMMARY OF THE INVENTION

According to one aspect of an embodiment, a nerve stimulating apparatus includes a plurality of stimulating units configured to respectively apply stimuli to a plurality of nerve regions branching from a particular nerve region of a living body, and a stimulation timing controller configured to set generating timings of respectively generating the stimuli at the plurality of stimulating units. The stimulation timing controller sets the generating timings of generating the stimuli at the plurality of stimulating units based on response results of the particular nerve region, the response results being obtained in response to the stimuli that are respectively generated at the plurality of stimulating units and that are respectively applied to the plurality of nerve regions, and the response results being measured by a biometric information measuring apparatus that measures biometric information.

DESCRIPTION OF THE EMBODIMENTS

Figure 1:
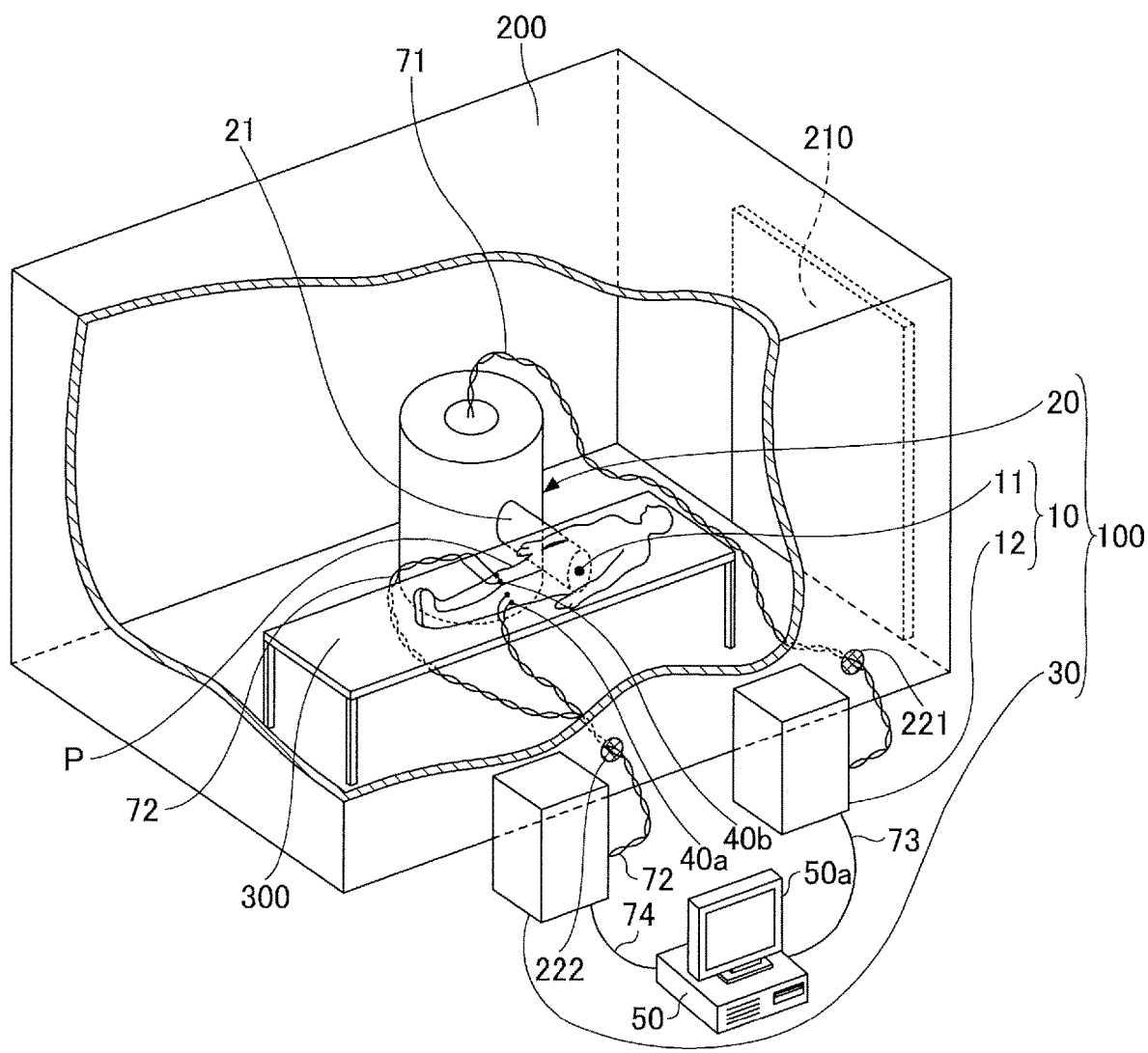
FIG. 1 is a system configuration diagram illustrating an example of a biometric information measuring system according to a first embodiment of the present invention.

The strength of the magnetic field signal being measured decreases as the distance from a region of applying an electrical stimulus to a region of measuring a magnetic field increases, because of the influence of temporal dispersion of electrical activities of the nerve. In the above-described technique, it may be difficult to accurately measure a magnetic field even when desired neural activities are induced using any one of multiple electrodes attached to close positions on a body surface.

The disclosed technique has been made in view of the above problem to be solved and aims to provide a method of applying stimuli to a living body that can increase the strength of the nerve activity of the living body.

According to one embodiment of the present disclosure, a method of applying stimuli to a living body that can increase the strength of the nerve activity of the living body can be provided.

In the following, embodiments will be described with reference to the drawings. In the drawings, the same components are referenced by the same reference numerals and overlapping descriptions may be omitted. In the following, a symbol representing a signal is also used as a symbol representing a signal value or a signal line (i.e., a cable).

First Embodiment

FIG. 1 is a system configuration diagram illustrating an example of a biometric information measuring system according to a first embodiment of the present invention. For example, a biometric information measuring system 100 illustrated in FIG. 1 is a spinal cord evoked magnetic field measuring system that measures a magnetic field generated from the spinal cord based on electrical stimuli.

The biometric information measuring system 100 includes a magnetic field measuring device 10, a cryogenic container 20, a nerve stimulating apparatus 30, and a data processing device 50 as major components. The nerve stimulating apparatus 30 is an apparatus that electrically stimulates nerves from a body surface (i.e., a skin) of a subject P.

The magnetic field measuring device 10 includes a superconducting quantum interference device (SQUID) sensor array 11 including multiple SQUIDs and a signal processing device 12. The magnetic field measuring device 10 can measure magnetic fields induced by nerves of the subject P to be measured in response to electrical stimuli of the nerve stimulating apparatus 30. The magnetic field measuring device 10 is an example of the biometric information measuring apparatus and is an example of a biomagnetic field measuring device. Hereinafter, a superconducting quantum interference element is also referred to as a SQUID.

The data processing device 50 has a function of performing information processing of biometric information, such as the magnetic fields measured by the magnetic field measuring device 10, and a function of controlling, for example, a timing of an electrical stimulus to the living body by the nerve stimulating apparatus 30. The data processing device 50 includes a display device 50a and has a function to display, for example, a waveform of the magnetic fields measured by the magnetic field measuring device 10 on the display device 50a. The data processing device 50 further includes an input device, such as a mouse or a keyboard, which is not illustrated.

A portion of the biometric information measuring system 100 is disposed in a magnetic shielding room 200 that shields magnetism. By using the magnetic shielding room 200, weak magnetic fields generated by the subject P (e.g., spinal cord evoked magnetic fields) can be measured. The magnetic shielding room 200 may be formed of, for example, a lamination of a plate material made of permalloy or the like, which is a high permeability material, and a plate material made of an electrical conductor, such as copper or aluminum.

The magnetic shielding room 200 has an internal space of about 2.5 m×3.0 m×2.5 m for example, and is provided with a door 210 that enables a device and equipment to be transported and persons to enter and exit. The door 210 may be formed of a laminate of a plate material made of permalloy or the like, which is a high permeability material and a plate material made of an electrical conductor, such as copper or aluminum, similarly with another part of the magnetic shielding room 200.

In the present specification, the high permeability material refers to a material having a relative permeability greater than 1000. Examples of the high permeability material include elemental substances of iron, nickel, and cobalt, alloys of these materials (including amorphous alloys, powders, and nanoparticles), and ferrites, in addition to permalloy.

In the following, the biometric information measuring system 100 and surrounding portions of the biometric information measuring system 100 will be described in more detail. In the magnetic shielding room 200, a table 300 is provided. Further, in the magnetic shielding room 200, the cryogenic container 20 is provided, and a signal line 71 used to measure a magnetic field and used for control at the measurement is connected to the SQUID sensor array 11 installed in the cryogenic container 20. The signal line 71 has a twisted cable structure to reduce magnetic field noise and is pulled out to outside of the magnetic shielding room 200 through a hole 221 formed through a wall of the magnetic shielding room 200 and connected to the signal processing device 12 constituting the magnetic field measuring device 10.

Measurement of spinal cord evoked magnetic fields using the biometric information measuring system 100 is performed on the subject P lying in the supine position on the table 300 placed in the magnetic shielding room 200 and being at rest. The measurement is performed in a rest state to not only reduce load of the subject P, but also reduce the displacement of the subject P from the SQUID sensor array 11 due to the movement of the subject P. Additionally, magnetic field noise from muscle caused by muscle tension is reduced, for example.

The cryogenic container 20, which is also referred to as the Dewar, holds liquid helium necessary to operate the SQUID sensor array 11, which detects magnetic fields generated by the subject P, at an extremely low temperature. The cryogenic container 20 includes, for example, protrusion 21 of a shape suitable for measuring the spinal cord evoked magnetic fields, and the SQUID sensor array 11 is provided in the protrusion 21. For example, the spinal cord evoked magnetic fields are measured in a state in which a waist of the subject P lying in the supine position is in contact with the protrusion 21 including the SQUID sensor array 11 inside.

When measuring the spinal cord evoked magnetic fields, it is necessary to deliberately induce nerve activities in the subject P by using the electrical stimulus. Thus, the electrical stimulus is applied using the nerve stimulating apparatus 30. For example, the nerve stimulating apparatus 30 includes electrodes 40a and 40b respectively attached to regions different from each other on the body surface of the subject P and can apply the electrical stimuli to the subject P from the electrodes 40a and 40b. Hereinafter, the electrodes 40a and 40b are also referred to as the electrodes 40 when the electrodes 40a and 40b are not distinguished in the following description.

In the example illustrated in FIG. 1, the electrode 40a is attached to a skin of a popliteal region of a left leg of the subject P and the electrode 40b is attached to a skin of a popliteal region of a right leg of the subject P, and the electrical stimuli applied from the electrodes 40a and 40b cause sciatic nerves of both legs of the subject P to be excited and cause nerve activities to be transmitted to a central nerve. The SQUID sensor array 11 facing a lumbar spine of the subject P detects the magnetic fields generated from the spinal cord and spinal nerves of the lumbar spine.

Each of the left and right sciatic nerves is one of peripheral nerve branches branching from the spinal cord, which is the central nerve. The central nerve is an example of a particular nerve region of the subject P, and the left and right sciatic nerves are examples of multiple nerve regions branching from the particular nerve region. The electrodes 40a and 40b are examples of multiple stimulating units that can generate electrical stimuli respectively applied to multiple nerve regions branching from the particular nerve region. The popliteal regions of both legs are examples of application regions to which the electrical stimuli are applied and that are positioned symmetrical with respect to the central nerve, which is a branch source of the peripheral nerve branches.

The electrodes 40a and 40b may be attached to regions that are on the skin of other regions where the sciatic nerves of the left and right legs pass and that are symmetrical with respect to the spinal cord and the spinal nerve of the lumbar spine, in which the magnetic field is measured. The magnetic field may be measured at the thoracic or cervical spine.

The electrodes 40a and 40b are connected to a main body of the nerve stimulating apparatus 30 (i.e., a part other than the electrodes 40a and 40b) provided outside the magnetic shielding room 200 through a signal line 72 for transmitting an electrical signal for stimulation. The signal line 72 has a twisted cable structure to reduce magnetic field noise. The signal line 72 is wired through a hole 222 formed through the wall of magnetic shielding room 200.

For example, the data processing device 50 is a computer device, such as a personal computer (PC), connected to a signal processing device 12 through a signal line 73 and connected to the nerve stimulating apparatus 30 through a signal line 74. The data processing device 50 controls an operation of the magnetic field measuring device 10, generates waveform data representing temporal changes of the biomagnetic field based on the measured data of the biomagnetic field transmitted from the signal processing device 12, and displays the waveform on the display device 50a using the generated waveform data. The data processing device 50 sets the timing of outputting the electrical stimuli from the electrodes 40a and 40b based on a measurement result of the biomagnetic field measured by the nerve stimulating apparatus 30 in the pre-measurement mode, which will be described later.

Figure 3:
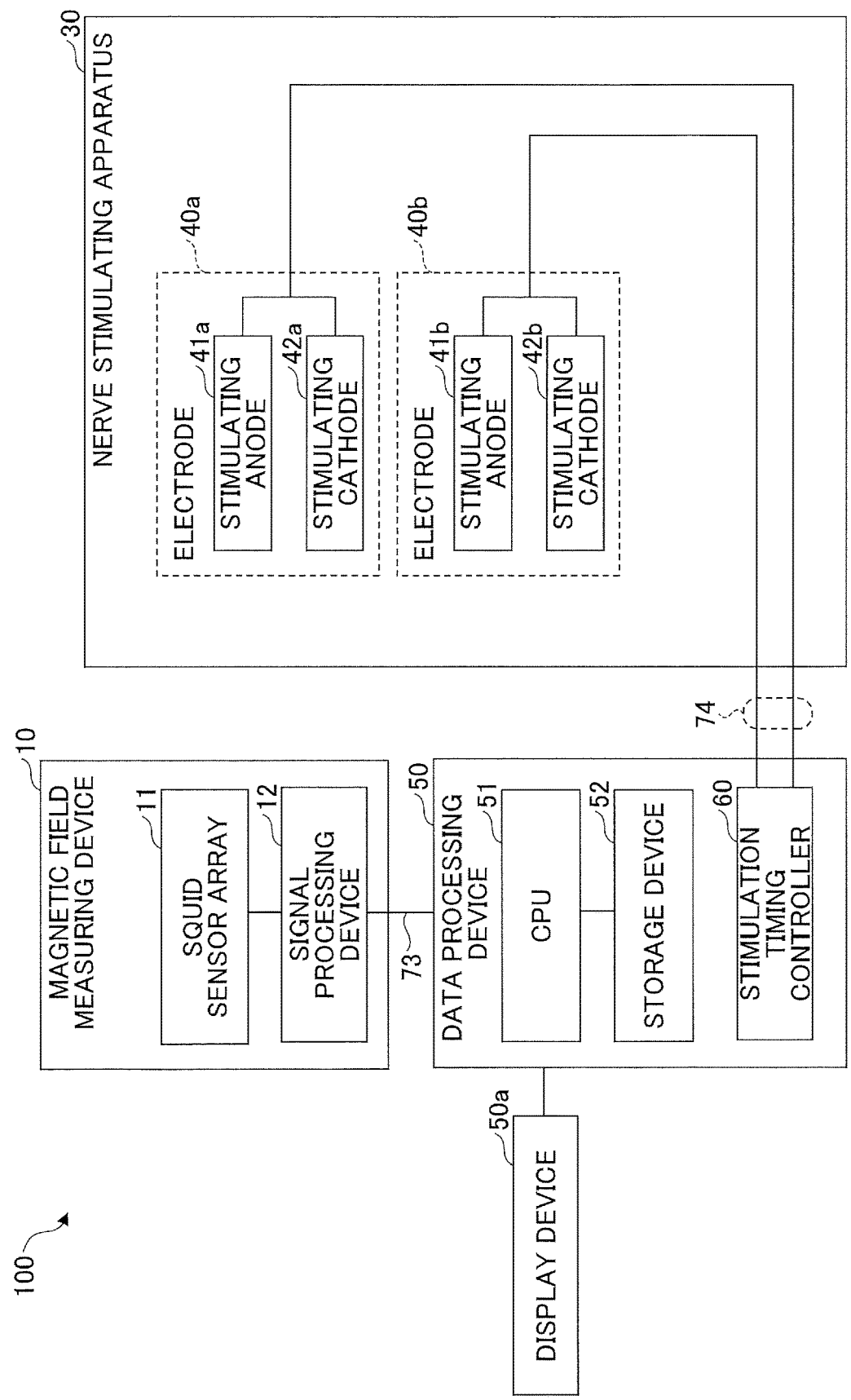
FIG. 3 is a functional block diagram illustrating another example of a main part of the biometric information measuring system illustrated in FIG. 1 and FIG. 2.

In order to induce the nerve activities of the subject P, the nerve stimulating apparatus 30, for example, applies a pulsed current between a stimulating anode 41a of the electrode 40a and a stimulating cathode 42a of the electrode 40a (FIG. 3) and applies a pulsed current between a stimulating anode 41b of the electrode 40b and a stimulating cathode 42b of the electrode 40b (FIG. 3). When measuring the spinal cord evoked magnetic fields, the nerve stimulating apparatus 30 applies a pulse current of, for example, the order of several mA and the order of several Hz, to the subject P as the electrical stimulus. The SQUID sensor array 11 detects induced magnetic fields from the spinal cord and the spinal nerve caused by the nerve activities induced by the electrical stimulus.

In general, nerve fibers branch from the center to the peripheries. In other words, the nerve fibers are merged from the peripheries toward the center. In the present embodiment, the electrical stimuli are applied to multiple application regions at branched peripheral nerves that are symmetrical to each other with respect to the central nerve at a timing when feature points of the magnetic field waveform appear at the same time, thereby increasing the strength of the magnetic field generated from the spinal cord or the like where the nerve fibers are merged. This enables the SQUID sensor array 11 to obtain a greater strength of the nerve activity magnetic field relative to a case of applying the electrical stimulus to the nerve fiber at a single region.

However, if the nerve activities induced by the electrical stimuli applied at multiple regions were not simultaneously transmitted to the measurement region of the magnetic field, the strength of the magnetic field generated from the measurement region would not be increased. If the nerve activities were not simultaneously transmitted to the measurement region of the magnetic field, the magnetic field generated at the measurement region based on the electrical stimulus applied to one of the peripheral nerves would appear as noise to the magnetic field generated at the measurement region based on the electrical stimulus applied to the other of the peripheral nerves.

The shape of the nerve fibers and the nerve activity that travels through the nerve fibers are not straight. Therefore, even when the electrical stimuli are applied simultaneously from the positions symmetrical to each other in the left and right legs, for example, the electrical stimuli are not necessarily transmitted simultaneously to the measurement region. Therefore, in the present embodiment, in order to simultaneously transmit the neural activities to the measurement region and increase the strength of the magnetic field output from the measurement region, respective timings of applying the electrical stimuli to the subject P from the electrodes 40a and 40b are set before the measurement of the magnetic field. That is, timings of generating electrical stimuli are set so that the phases of the nerve electrical activities are matched at a junction of the nerves, which is the measurement region. A method of setting the timings of applying the electrical stimuli will be described in FIG. 3 and later.

Figure 2:
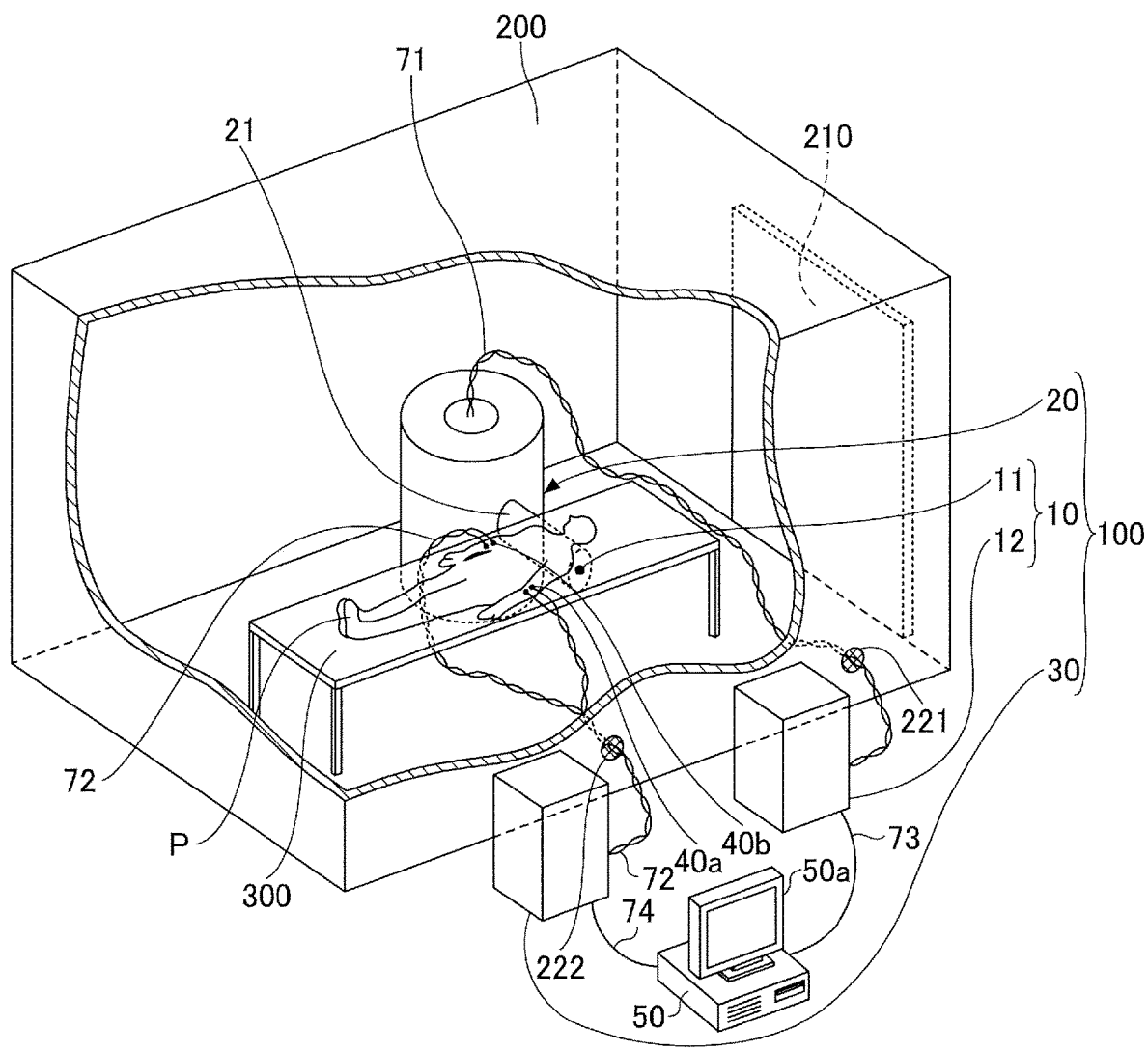
FIG. 2 is a system configuration diagram illustrating another example of the biometric information measuring system according to the first embodiment of the present invention.

FIG. 2 is a system configuration diagram illustrating another example of the biometric information measuring system 100 according to the first embodiment of the present invention. For the same elements as in FIG. 1, a detailed description will be omitted. In FIG. 2, the biometric information measuring system 100 is a spinal cord evoked magnetic field measuring system.

In the biometric information measuring system 100 illustrated in FIG. 2, the SQUID sensor array 11 is provided facing the cervical spine of the subject P being in the supine position at the table 300 to detect the magnetic fields generated from nerve fibers in the cervical spine.

In this case, for example, the electrodes 40a and 40b are respectively attached to a left elbow and right elbow, and the electrical stimuli applied by the electrodes 40a and 40b induce median nerves in the left and right arms and are transmitted to the nerve fibers passing through the cervical spine.

The median nerves, which pass through the left and right elbows, are one of the branches of the peripheral nerves that branches from the spinal cord, which is the central nerve. The median nerves passing through the left and right elbow are examples of multiple nerve regions that branch from the particular nerve region. The left elbow and the right elbow are examples of application regions to which electrical stimuli are applied at positions symmetrical to each other with respect to the central nerve, which is the branch source of the peripheral nerves.

FIG. 2 is similar to FIG. 1 except that a positional relationship between the SQUID sensor array 11 and the subject P is different and the application regions to which the electrodes 40a and 40b are attached are different. Also in FIG. 2, the timings of generating the electrical stimuli are set so that the phases of nerve electrical activities are matched at the junction of the nerves, which is the measurement region of the spinal cord. A method of setting the timings of generating the electrical stimuli so that the phases of nerve electrical activities are matched at the junction of nerves, which is the measurement region of the spinal cord, will be described in FIG. 3 and later.

The following description may be applied to an example in which the electrical stimuli are applied to the popliteal regions of both legs of the subject P illustrated in FIG. 1, or to an example in which the electrical stimuli are applied to the left and right elbows of the subject P illustrated in FIG. 2. Further, the following description is not limited to the popliteal regions and the left and right elbows, but may be applied to an example in which the electrical stimuli are applied to two nerve regions branching from the particular nerve region of the subject P (e.g., fingers of the hand).

FIG. 3 is a functional block diagram illustrating an example of a main part of the biometric information measuring system 100 (i.e., the spinal cord evoked magnetic field measuring system) illustrated in FIGS. 1 and 2. The nerve stimulating apparatus 30 includes the electrode 40a including the stimulating anode 41a and the stimulating cathode 42a, and the electrode 40b including the stimulating anode 41b and the stimulating cathode 42b. For example, the nerve stimulating apparatus 30 includes only the electrodes 40a and 40b, and the electrodes 40a and 40b receiving current from the outside function as the nerve stimulating apparatus 30. For example, a commercial product (i.e., a general purpose product) may be used as the nerve stimulating apparatus 30.

The data processing device 50 includes a CPU 51, a storage device 52, and a stimulation timing controller 60. The stimulation timing controller 60 is an example of a stimulation timing control device. The CPU 51 executes, for example, a measurement control program stored in the storage device 52 to control an operation of the magnetic field measuring device 10. The CPU 51 executes a stimulation timing setting program stored in the storage device 52 to control the stimulation timing controller 60 and sets the timings of generating the electrical stimuli generated from the electrodes 40a and 40b. The stimulation timing controller 60 can apply the electrical stimulus (e.g., a current pulse) to each of the electrodes 40a and 40b at any timing. The following description assumes that a specification of the electrical stimulus (e.g., a current value, a frequency, and a connecting duration) is predetermined.

The biometric information measuring system 100 has a normal measurement mode in which the electrical stimuli are applied to multiple regions of the subject P by using both electrodes 40a and 40b to diagnose a disease or the like. The biometric information measuring system 100 also has a pre-measurement mode in which the electrical stimulus is individually applied to the subject P by using each of the electrodes 40a and 40b to cause the SQUID sensor array 11 to measure the magnetic field before measuring the magnetic field in the normal measurement mode.

The stimulation timing controller 60 applies the electrical stimulus only to the electrode 40a attached to the body surface of the subject P, for example, in a pre-measurement mode. The SQUID sensor array 11 measures a magnetic field generated from the nerve of the subject P in response to the electrical stimulus from the electrode 40a and outputs a magnetic field signal representing the measured magnetic field to the signal processing device 12. The signal processing device 12 performs signal processing on the magnetic field signal received from the SQUID sensor array 11 to generate magnetic field data (i.e., waveform data) and stores the generated magnetic field data in the storage device 52. For example, the magnetic field data is waveform data representing temporal changes in the magnetic field strength.

Next, the stimulation timing controller 60 applies an electrical stimulus to the electrode 40b attached to the body surface of the subject P, for example. The SQUID sensor array 11 measures a magnetic field generated from the nerve of the subject P in response to the electrical stimulus from the electrode 40b and outputs a magnetic field signal representing the measured magnetic field to the signal processing device 12. The signal processing device 12 performs signal processing on the magnetic field signal received from the SQUID sensor array 11 to generate magnetic field data (i.e., waveform data) and stores the generated magnetic field data in the storage device 52.

Next, the stimulation timing controller 60 extracts feature points of the response waveforms, such as peak latency or rise latency, using the waveform data respectively generated in response to the electrical stimuli applied by the electrodes 40a and 40b. Here, the peak latency is the duration from when the electrical stimuli are applied to when the magnetic field strength becomes a maximum value or a minimum value. The rise latency is the duration to when the magnetic field strength changes toward a maximum value, and, is for example, the duration to when the magnetic field strength changes from negative to positive (e.g., the duration until the magnetic field strength crosses zero).

As described above, the stimulation timing controller 60 calculates latency from an application of the stimulation to a response of the central nerve (i.e., a feature point) in each of the electrodes 40a and 40b, based on a response at the measurement region measured by the magnetic field measuring device 10 in response to the stimulus at each of the application regions of the subject P. The peak latency and the rise latency will be described in FIGS. 4 to 7.

The stimulation timing controller 60 sets the timings of generating the electrical stimuli applied by the electrodes 40a and 40b so that a feature point of the response waveform corresponding to the electrode 40a and a feature point of the response waveform corresponding to the electrode 40b appear at the same time. For example, the stimulation timing controller 60 delays the timing of generating the electrical stimulus through the electrode 40 that corresponds to the response waveform in which the feature point appears earlier, thereby matching timings when the feature points appear. That is, the stimulation timing controller 60 sets the timings of generating the electrical stimuli through the electrodes 40a and 40b to timings that match timings when the feature points appear, based on the latency calculated in the pre-measurement mode. Hereinafter, the timing of the electrical stimulus is also referred to as a stimulus generating timing.

The stimulation timing controller 60 uses the timings of the electrical stimuli applied by the electrodes 40a and 40b determined in the pre-measurement mode to generate the electrical stimuli at the electrodes 40a and 40b when the magnetic fields are measured in the normal measurement mode. The magnetic field measuring device 10 detects magnetic fields generated by the nerves of the subject P in response to the electrical stimuli through the electrodes 40a and 40b.

In this case, the timings of the feature points (i.e., the peak latency or the rise latency) of the magnetic field strength waveforms respectively corresponding to the electrodes 40a and 40b can be matched to each other by the stimulus generating timings set in the pre-measurement mode. Therefore, in comparison with a case in which the electrical stimulus is applied from only the single electrode 40, a large magnetic field strength can be obtained, and the measurement accuracy of the magnetic fields generated from the subject P by using the biometric information measuring system can be improved.

Additionally, because a large magnetic field strength is obtained, it is possible to increase the distance between the application region to which the electrical stimulus is applied and the region at which the magnetic field is measured relative to a conventional method. As a result, it is possible to measure the magnetic field generated from a region where it has been difficult to measure in the past. The stimulation timing controller 60 may be disposed in the signal processing device 12 of the magnetic field measuring device 10 instead of the data processing device 50.

Figure 4:
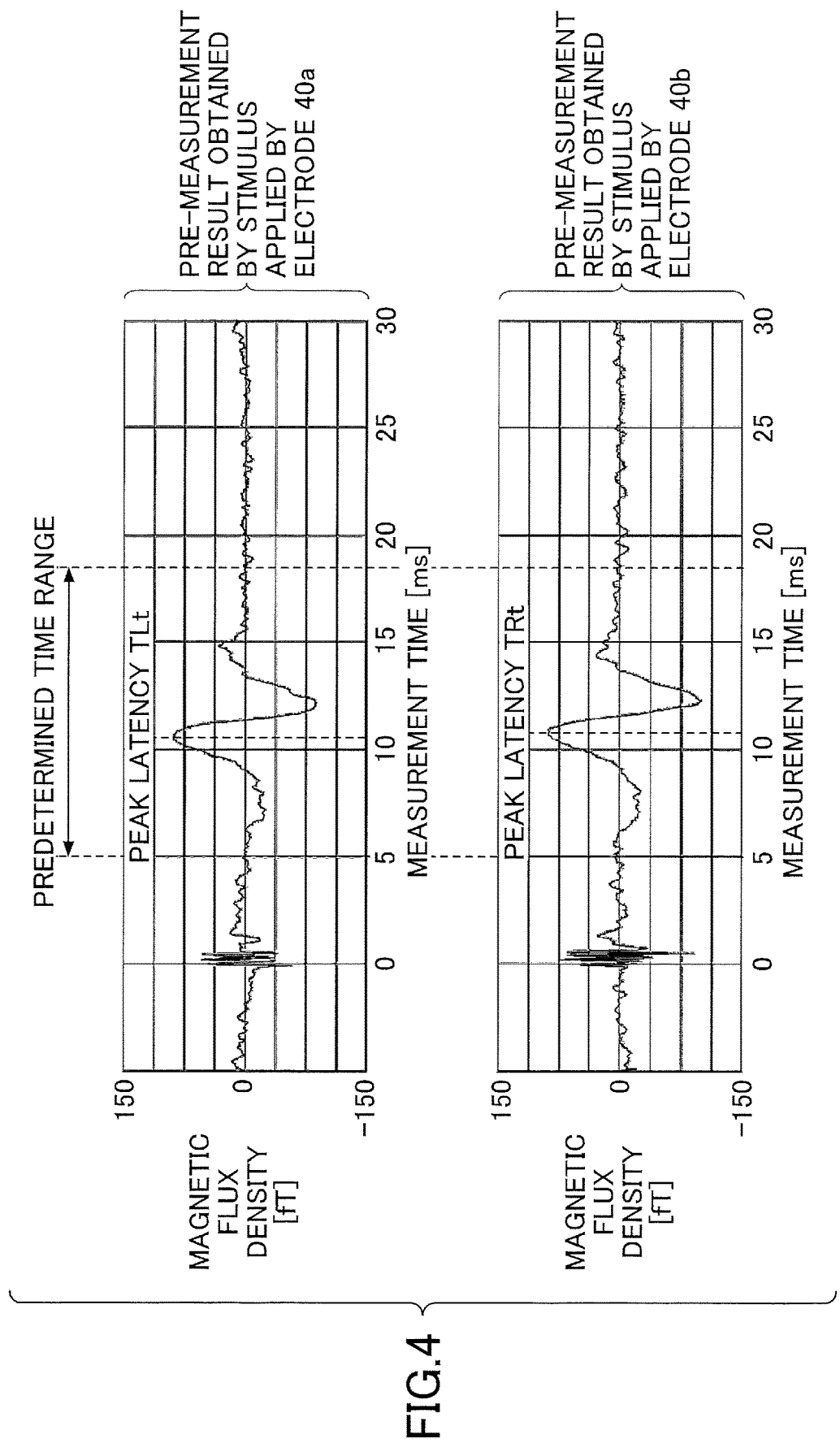
FIG. 4 is an explanatory drawing illustrating an example of a process of a pre-measurement mode in the biometric information measuring system illustrated in FIG. 3.
Figure 5:
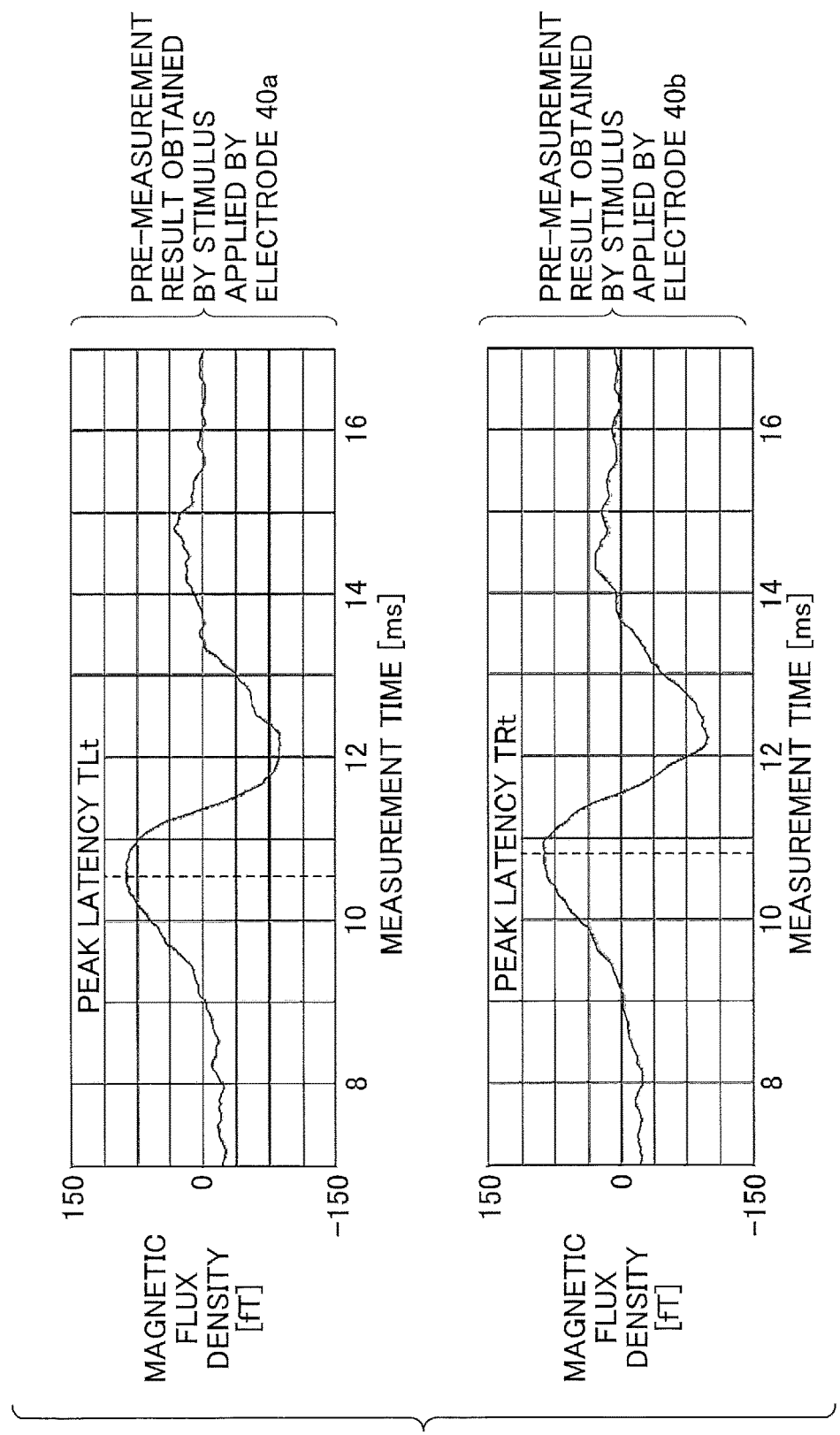
FIG. 5 is a waveform drawing enlarged around peak latency of the waveform in FIG. 4.

FIG. 4 is an explanatory drawing illustrating an example of a process of the pre-measurement mode in the biometric information measuring system 100 of FIG. 3, and FIG. 5 is a waveform drawing enlarged around the peak latency of the waveform of FIG. 4. The horizontal axis of the waveform illustrated in FIGS. 4 and 5 indicates the measurement time [ms] of the magnetic field strength measured by the SQUID sensor array 11. Here, 0 ms in the measurement time indicates time at which the electrical stimulus is applied to the living body from the electrode 40. The vertical axis of the waveform illustrated in FIGS. 4 and 5 indicates the strength of the magnetic field (i.e., the magnetic flux density [fT]) generated by the subject P measured by the SQUID sensor array 11.

The upper waveform in FIG. 4 illustrates an example of changes in the strength of the magnetic field measured by the SQUID sensor array 11 in response to the electrical stimulus applied from the electrode 40a attached to the subject P in the pre-measurement mode. The lower waveform in FIG. 4 illustrates an example of changes in the strength of the magnetic field measured by the SQUID sensor array 11 in response to the electrical stimulus applied from the electrode 40b attached to the subject P in the pre-measurement mode. That is, FIG. 4 illustrates the magnetic field measurement data obtained by the SQUID sensor array 11 in response to the electrical stimuli applied from the electrodes 40a and 40b.

The upper waveform in FIG. 4 and the lower waveform in FIG. 4 are aligned with respect to the time axis, but the magnetic field is measured at different times. That is, the measurement of the magnetic field for obtaining the upper waveform of FIG. 4 and the lower waveform of FIG. 4 is performed by generating the electrical stimulus through each of the electrodes 40a and 40b at different timings. After the two waveform data are obtained, the CPU 51 displays the two waveform data vertically arranged on the display device 50a with a dashed line indicating the time range and a dashed line indicating the peak latency as illustrated in FIG. 4.

In the example illustrated in FIG. 1, the electrode 40a is attached to the popliteal region of the left leg of the subject P, the electrical stimulus from the electrode 40a excites the sciatic nerve of the left leg, and the nerve activity is transmitted to the spinal cord. The electrode 40b is attached to the popliteal region of the right leg of the subject P, the electrical stimulus from the electrode 40b excites the sciatic nerve of the right leg, and the nerve activity is transmitted to the spinal cord.

In the example illustrated in FIG. 2, the electrode 40a is attached to the left elbow of the subject P, the electrical stimulus from the electrode 40a excites the median nerve of the left arm, and the nerve activity is transmitted to the spinal cord. The electrode 40b is attached to the right elbow of the subject P, the electrical stimulus from the electrode 40b excites the median nerve in the right arm, and the nerve activity is transmitted to the spinal cord.

In FIG. 4, the stimulation timing controller 60 can calculate measurement time of peaks (i.e., a peak value on a positive side) in which the height of each of two waveforms included in a predetermined time range is maximum, as peak latency TLt and TRt. The peak latency TLt and TRt is the duration from when the electrical stimulus is applied to when the peak of the waveform appears and depends on the distance between the application region of stimulation and the measurement region of the magnetic field.

However, because a travel of the nerve is not a straight line, and the speed at which the stimulation transmits through the nerve varies slightly in each nerve, it is difficult to accurately measure the distance from the appearance using a measure or the like. Therefore, it is difficult to match timings at which the peak latency TLt and TRt appear by adjusting attached positions of the electrodes 40a and 40b based on the measurement from the appearance. In the present embodiment, the timings when the peak latency TLt and TRt appear can be matched by adjusting timings of generating the electrical stimuli from the electrodes 40a and 40b.

The "predetermined time range" illustrated in FIG. 4 is set to exclude, from the calculation of the peak latency TLt and TRt, a noise waveform (e.g., around 0 ms) generated by the electrical stimuli applied to the subject P from the electrodes 40a and 40b. For example, the predetermined time range is set by an operator of the biometric information measuring system 100 by specifying a time range of the measurement waveform displayed on the display device 50a by using an input device, such as a mouse.

The predetermined time range may be automatically set by a program executed by the CPU 51. The distance from the application region to which the electrical stimulus is applied to the measurement region of the magnetic field approximately depends on the height of the subject P and the length of the legs of the subject P. Therefore, the CPU 51 can automatically set the time range based on the height of the subject P and the length of the legs of the subject P input from the input device, such as a keyboard, by an operator or the like.

In this case, the time range may be estimated by the CPU 51 by accumulating information such as the height and the length of the legs of other subjects P of whom the magnetic field has been measured in the past and a combination of the time range and the peak latency, and using the accumulated information. The estimation of the time range may be performed using machine learning techniques. By using information about magnetic field measurement in the past, the accuracy of time range setting can be improved in comparison with simply setting the time range using a calculation formula.

The stimulation timing controller 60 determines that the peak latency TLt and TRt match when a shift between the peak latency TLt and TRt is, for example, 0.1 ms or smaller. A threshold of the shift used to determine whether the peak latency TLt and TRt match is not limited to 0.1 ms, but may be 0.05 ms or 0.01 ms, for example. Preferably, the threshold is greater than or equal to minimum setting time for a difference in generating the electrical stimuli through the electrodes 40a and 40b that can be set by the nerve stimulating apparatus 30. For example, the minimum time for the difference in generating the electrical stimuli set by the nerve stimulating apparatus 30 is 0.01 ms.

As illustrated in FIG. 5, when the peak latency TLt and the peak latency TRt do not match, the stimulation timing controller 60 delays the timing of generating the electrical stimulus generated from one of the electrodes 40a and 40b in order to match the timings when the peak latency TLt and the peak latency TRt appear.

The stimulation timing controller 60, for example, determines to delay the stimulus generating timing of the electrode 40a by the time difference between the peak latency TLt and the peak latency TRt when the peak latency TLt is earlier than the peak latency TRt. In the example of FIG. 5, it is determined that the timing of the electrical stimulus generated from the electrode 40a is delayed by 0.2 ms relative to the timing of the electrical simulation generated from the electrode 40b.

Similarly, the stimulation timing controller 60 determines to delay the stimulus generating timing of the electrode 40b by the time difference between the peak latency TLt and the peak latency TRt when the peak latency TRt is earlier than the peak latency TLt, for example. When the peak latency TLt and peak latency TRt match, the stimulation timing controller 60 determines to use the stimulus generating timings of the electrodes 40a and 40b used in the pre-measurement mode, in the normal measurement mode.

The stimulation timing controller 60 uses the determined stimulus generating timings in the normal measurement mode. That is, the stimulation timing controller 60 sets the stimulus generating timings of the electrodes 40a and 40b so as to cause the peak latency TLt and peak latency TRt to be at the same time, based on the latency calculated for each of the electrodes 40a and 40b in the pre-measurement mode.

Figure 6:
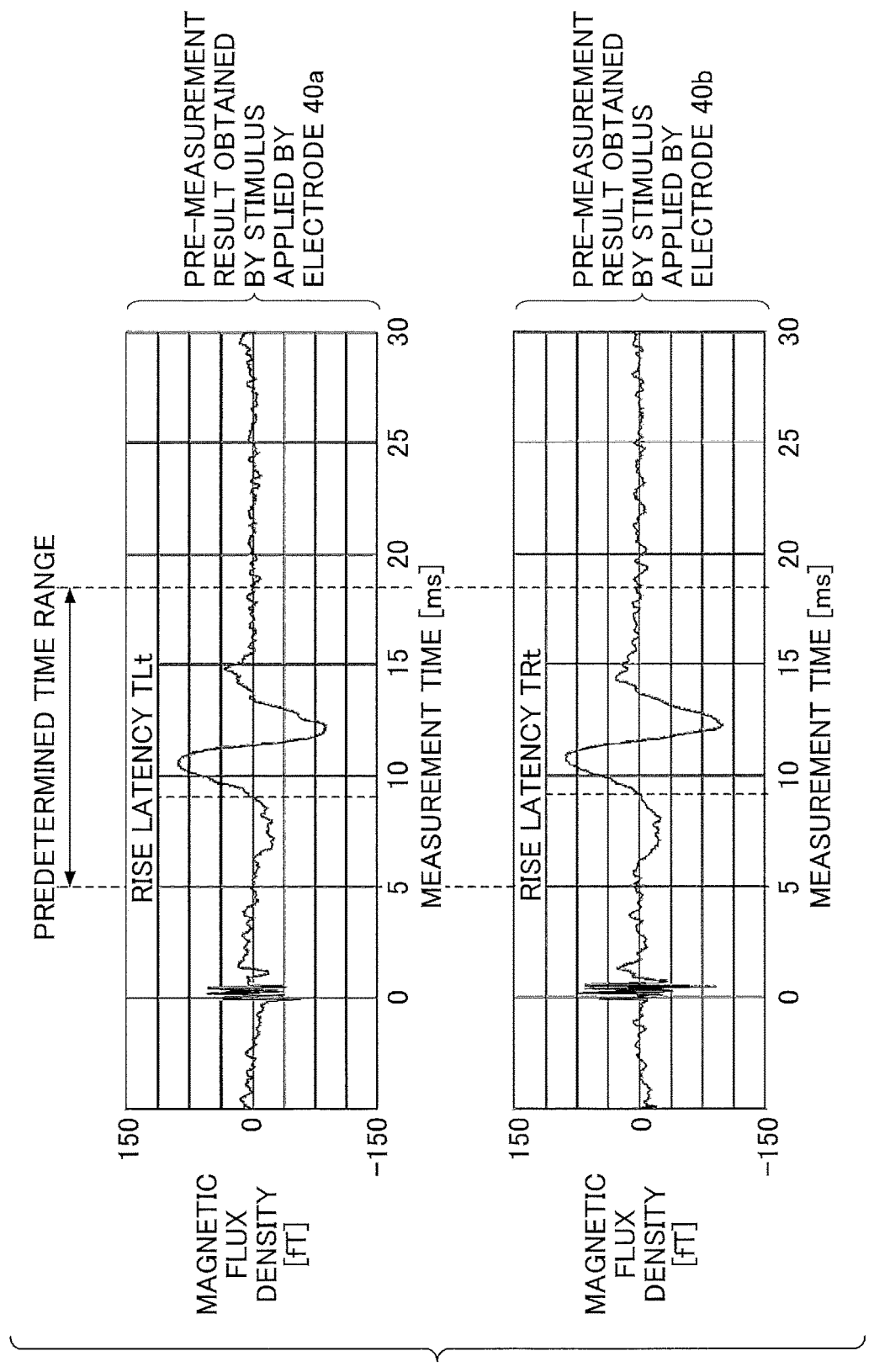
FIG. 6 is an explanatory drawing illustrating another example of the process of the pre-measurement mode in the biometric information measuring system illustrated in FIG. 3.

FIG. 6 is an explanatory drawing illustrating another example of the process of the pre-measurement mode in the biometric information measuring system illustrated in FIG. 3. For the same elements and processes as illustrated in FIG. 4, the detailed description will be omitted.

In FIG. 6, the stimulation timing controller 60 calculates measurement time at rising when the strength of the magnetic field of each of two waveforms included in the predetermined time range changes from negative to positive as the latency TLt and the latency TRt. Then, the stimulation timing controller 60 delays a timing of the electrical stimulus generated from one of the electrodes 40a and 40b in order to match timings when the rise latency TLt and the rise latency TRt appear in accordance with the time difference between the rise latency TLt and the rise latency TRt, similarly with FIG. 4.

The set stimulus generating timing is used in the normal measurement mode. Similarly with the description of FIG. 4, when the rise latency TLt and the rise latency TRt match in the pre-measurement mode, the stimulus generating timings of the electrodes 40a and 40b used in the pre-measurement mode are used in the normal measurement mode.

Also in FIG. 6, after waveform data of two waveforms is obtained, the CPU 51 displays the two waveforms data vertically on the display device 50a with a dashed line indicating the time range and a dashed line indicating the rise latency.

Figure 7:
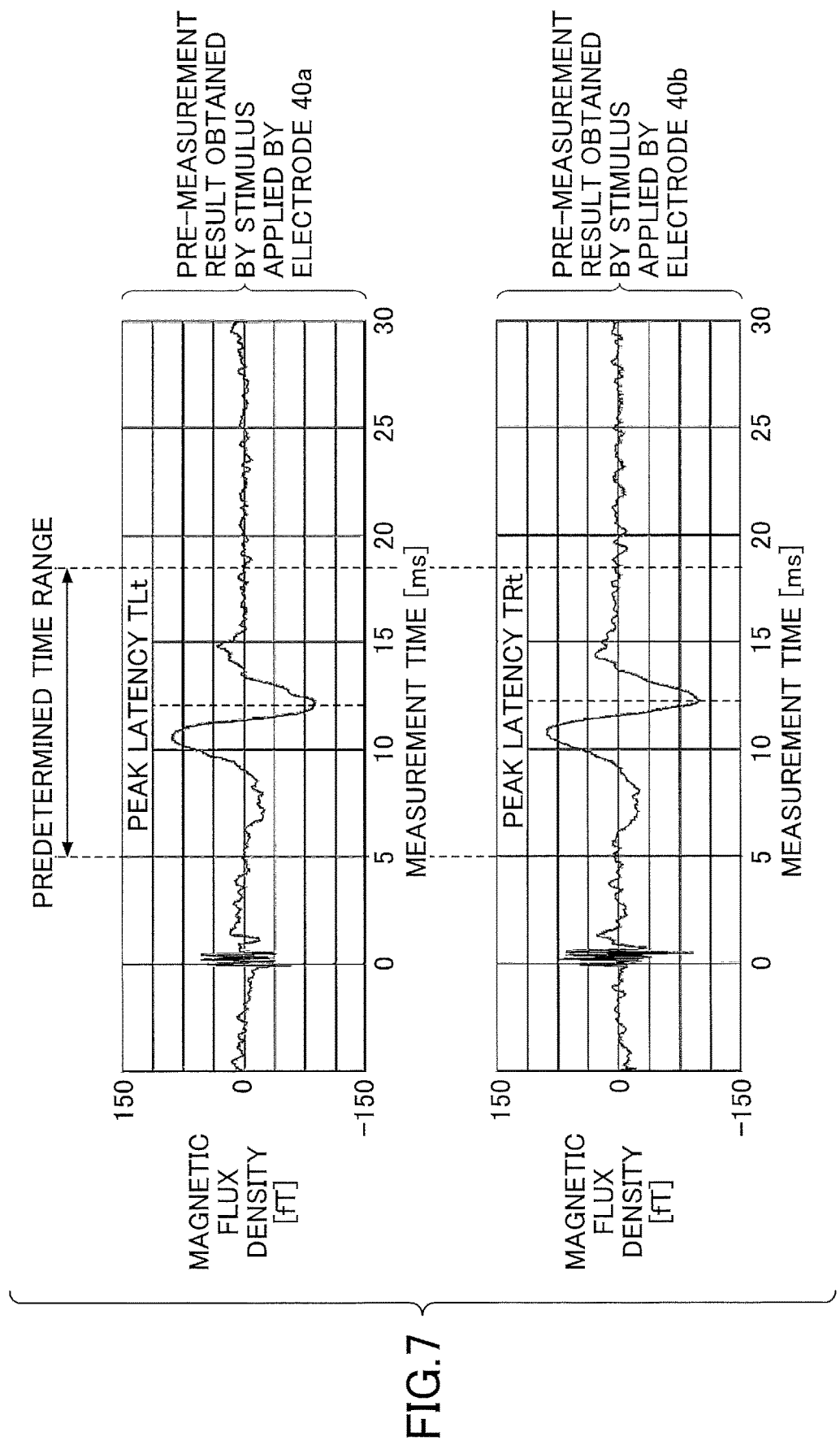
FIG. 7 is an explanatory drawing illustrating yet another example of the process of the pre-measurement mode in the biometric information measuring system illustrated in FIG. 3.

FIG. 7 is an explanatory drawing illustrating yet another example of the process of the pre-measurement mode in the biometric information measuring system 100 of FIG. 3. For the same elements and processes as illustrated in FIG. 4, the detailed description will be omitted.

In FIG. 7, the stimulation timing controller 60 calculates measurement time of a peak (i.e., a peak value on a negative side) in which the height of each of the two waveforms included in the predetermined time range is the smallest, as the peak latency TLt and the peak latency TRt. Then, the stimulation timing controller 60 sets the stimulus generating timings of the electrodes 40a and 40b in order to match timings of the peak latency TLt and the peak latency TRt in accordance with the time difference between the peak latency TLt and the peak latency TRt as in FIG. 4. The set stimulus generating timings are used in the normal measurement mode. Similarly with the description of FIG. 4, when the peak latency TLt and the peak latency TRt match in the pre-measurement mode, the stimulus generating timings of the electrodes 40a and 40b used in the pre-measurement mode are used in the normal measurement mode.

Also in FIG. 7, after the waveform data of the two waveforms is obtained, the CPU 51 displays the two waveforms data vertically on the display device 50a with a dashed line indicating the time range and a dashed line indicating the peak latency.

In the pre-measurement mode, whether the latency is a peak latency or a rise latency may be determined in accordance with an environment in which the magnetic field is measured. For example, when a signal-to-noise ratio (SN ratio) decreases because measured environmental magnetic field (i.e., artifact) is larger than the strength of the biomagnetic field, it is preferable to obtain a temporal feature amount of the waveform at the peak latency. Calculation of the latency by using the rise latency is a method commonly used in the field of electrophysiology.

In FIGS. 4, 6 and 7, an example in which the stimulation timing controller 60 automatically calculates the peak latency or the rise latency has been described. However, for example, the biometric information measuring system 100 may be provided with a manual setting mode and the peak latency or the rise latency may be specified by an operator or the like viewing the display device 50a on which two waveforms of the magnetic field are displayed. Alternatively, the peak latency or the rise latency may be adjusted by the operator using a mouse or the like to move the dashed line indicating the peak latency or the rise latency calculated by the stimulation timing controller 60 and displayed on the display device 50a in the time axis direction. At this time, as illustrated in FIG. 5, the waveform displayed on the display device 50a may be enlarged in the time axis direction.

Figure 8:
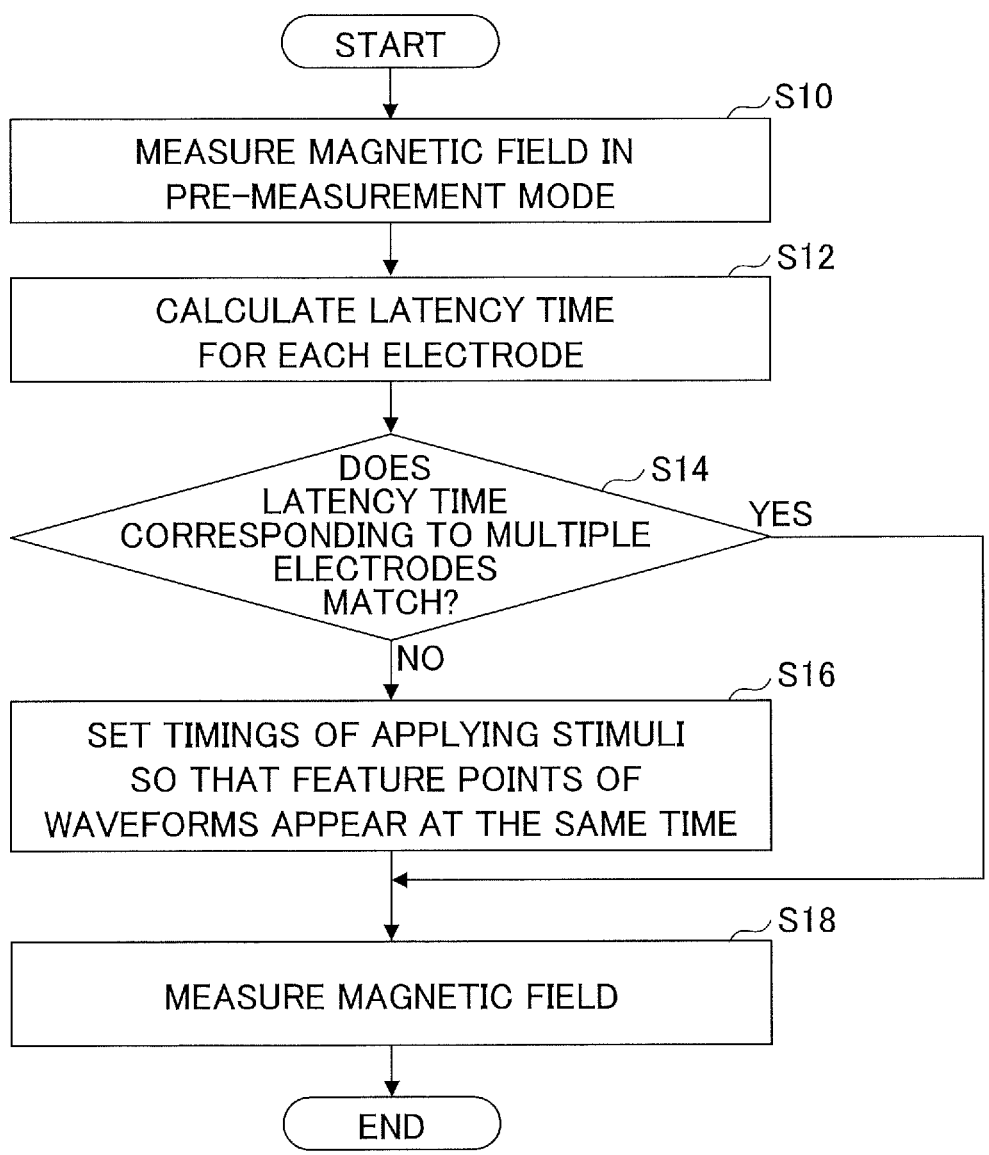
FIG. 8 is a flowchart illustrating an example of a measurement operation of a magnetic field in the biometric information measuring system illustrated in FIG. 3.

FIG. 8 is a flowchart illustrating an example of a measurement operation of a magnetic field in the biometric information measuring system 100 in FIG. 3. In FIG. 8, steps S10, S12, S14, and S16 depict an example of a method of setting the stimulus generating timing of the biometric information measuring system, and the CPU 51 and the stimulation timing controller 60 cooperate in the pre-measurement mode to perform the method.

In step S10, the biometric information measuring system 100 respectively generates the stimuli on the electrodes 40a and 40b as described above and measures the magnetic fields in the pre-measurement mode.

Next, in step S12, the biometric information measuring system 100 calculates the latency for each of the electrodes 40a and 40b by using any one of the methods illustrated in FIG. 4, FIG. 6, or FIG. 7 based on magnetic field measurement results in step S10.

Next, in step S14, the biometric information measuring system 100 determines whether latency corresponding to the electrode 40a and latency corresponding to the electrode 40b match. When the latency matches, the biometric information measuring system 100 performs step S18. When the latency does not match, the biometric information measuring system 100 performs step S16. As described above, matching/non-matching is determined, for example, by whether the latency difference is 0.1 ms or smaller.

In step S16, the biometric information measuring system 100 sets the generating timings of generating the electrical stimuli at the electrodes 40a and 40b so that the feature points of the waveforms appear at the same time, and performs step S18. For example, the stimulus generating timing is adjusted by delaying the stimulus generating timing of the electrode 40 corresponding to early latency shifted by the latency difference. That is, the stimulus generating timing of only one of the electrodes 40a and 40b is delayed.

In step S14 and step S16, by adjusting the stimulus generating timing, the magnetic fields generated from the spinal cord or the like can be accurately overlapped in response to the electrical stimuli applied from the electrodes 40a and 40b, thereby increasing the magnetic field strength. This can prevent the magnetic field strength from being weakened even when positions on the skin of the subject P to which the electrodes 40a and 40b attached are shifted from ideal positions. In other words, the positions on the skin of the subject P to which the electrodes 40a and 40b are attached may not be required to be precisely determined, thus the workability of the preparation before measuring the magnetic field can be improved.

In step S18, the biometric information measuring system 100 transitions from the pre-measurement mode to the normal measurement mode, and applies the electrical stimuli to the subject P from the electrodes 40a and 40b to measure the magnetic field generated by the subject P. Then, the measurement operation of the biomagnetic field performed by the biometric information measuring system 100 is terminated.

For example, in step S18, when the magnetic field strength is lowered while repeatedly applying the electrical stimuli to the subject P to measure the magnetic field, the electrode 40 attached to the application region may be misaligned due to the movement of the subject P on the table 300. In this case, the measurement operation of the magnetic field may be stopped once, and the process illustrated in FIG. 8 may be performed again.

Figure 9:
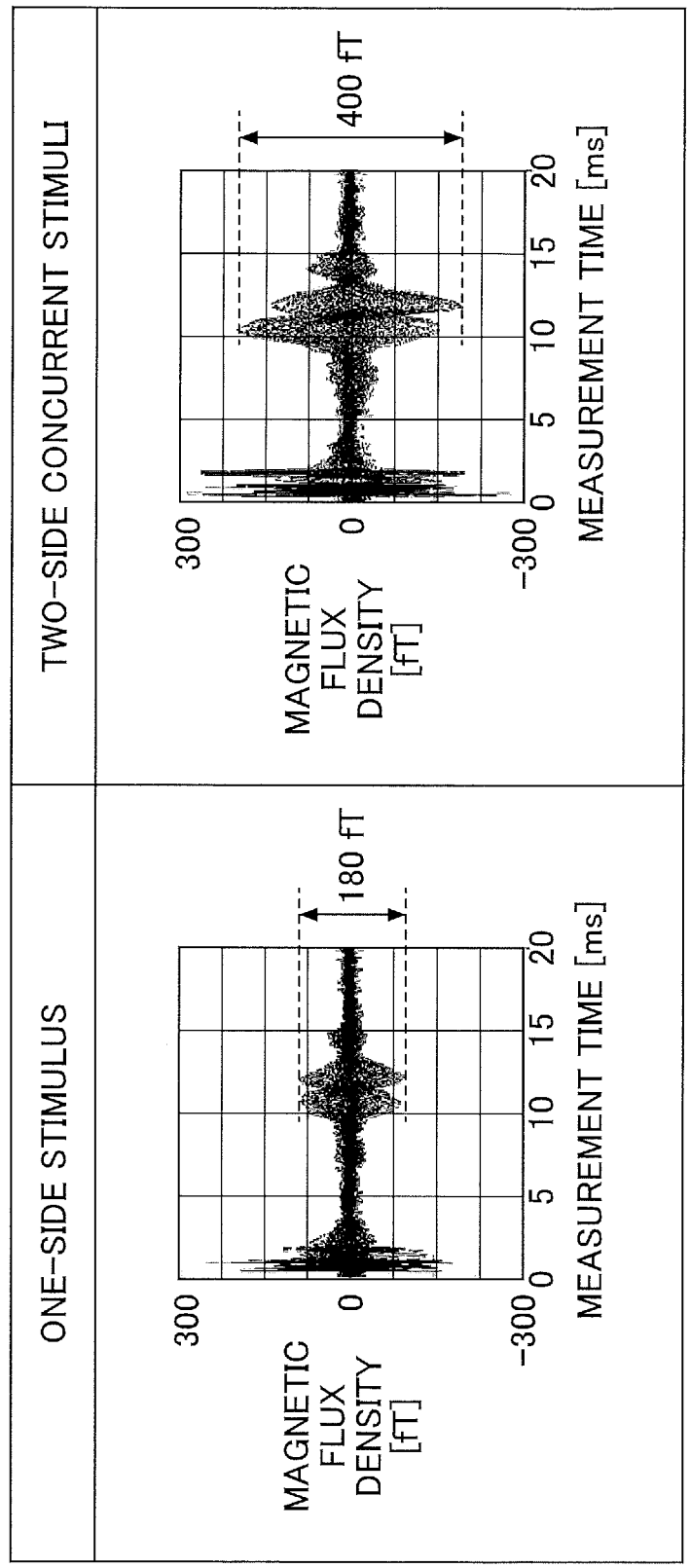
FIG. 9 is a waveform drawing illustrating an example of temporal changes of the strength of a magnetic field signal in one-side stimulus and two-side concurrent stimuli in the biometric information measuring system illustrated in FIG. 3.

FIG. 9 is a waveform drawing illustrating an example of temporal changes in the strength of a magnetic field signal in one-side stimulus and two-side concurrent stimuli in the biometric information measuring system 100 of FIG. 3. The one-side stimulus illustrates a waveform obtained when the electrical stimulus is applied to the subject P by using one of the electrodes 40a and 40b. The two-side concurrent stimuli illustrate a waveform obtained when the electrical stimuli are applied simultaneously to the subject P from the electrodes 40a and 40b using the stimulus generating timing determined in the pre-measurement mode, in the normal measurement mode. The waveforms of the magnetic field illustrated in FIG. 9, for example, are overlapped by the magnetic fields measured by multiple SQUIDs of the SQUID sensor array 11.

In the example illustrated in FIG. 9, the strength of the magnetic field (i.e., 400 fT) obtained by the two-side concurrent stimuli is approximately twice the strength of the magnetic field (i.e., 180 fT) obtained by the one-side stimulus. That is, it is found that by using the stimulus generating timing determined in the pre-measurement mode to generate the electrical stimuli from the electrodes 40a and 40b, the measured strength of the magnetic field is increased. Therefore, when the application region is away from the measurement region, such as when the electrical stimulus is applied to the popliteal region to measure a magnetic field generated by the thoracic spinal cord, the magnetic field strength being measured can be increased relative to a conventional method. As a result, it is possible to measure the magnetic field at the measurement region at which the measurement is difficult using a conventional method.

As described, in the present embodiment, the stimulus generating timings of the electrodes 40a and 40b are set based on response results of a particular nerve region in response to the stimulus applied to each of multiple nerve regions branching from the particular nerve region. For example, the stimulus generating timings of the electrodes 40a and 40b are set based on a measurement result of the magnetic field generated from the particular region of the central nerve in response to the electrical stimulus applied to each of multiple nerve regions of the peripheral nerves branching from the spinal cord (i.e., the central nerve).

By using the set stimulus generating timings to generate the stimulation in parallel from both electrodes 40a and 40b, the strength of the magnetic field generated from the spinal cord where the nerve fibers join can be increased. This enables the SQUID sensor array 11 to obtain a larger magnetic field strength generated by the nerve activity in comparison with a case of applying the electrical stimulus to the nerve fiber at a single region. That is, a timing of generating the stimuli to the living body that can increase the strength of the nerve activity of the living body can be set.

By extracting the feature point of the response waveform of the magnetic field in response to the electrical stimulus by using the peak latency or the rise latency, the correct latency can be determined regardless of the shape of the waveform. This can accurately set the stimulus generating timings of the electrodes 40a and 40b to match the timings at which the feature points appear. The magnetic field strength can be further increased because the timings at which the feature points appear can accurately match.

The magnetic field strength can also be prevented from being weakened when positions on the skin of the subject P to which the electrodes 40a and 40b are attached are shifted from the ideal positions. In other words, the positions of the electrodes 40a and 40b on the skin of the subject P may not be required to be precisely determined, and the workability of the preparation before measuring the magnetic field can be improved.

By providing the stimulation timing controller 60 that obtains the stimulus generating timings of the electrodes 40a and 40b in the data processing device 50, an existing nerve stimulating apparatus 30 can be used to apply the electrical stimuli to the electrodes 40a and 40b at timings that increase the magnetic field strength. For example, a commercially available nerve stimulating apparatus 30 can be used to reduce the cost of the biometric information measuring system 100.

Second Embodiment

Figure 10:
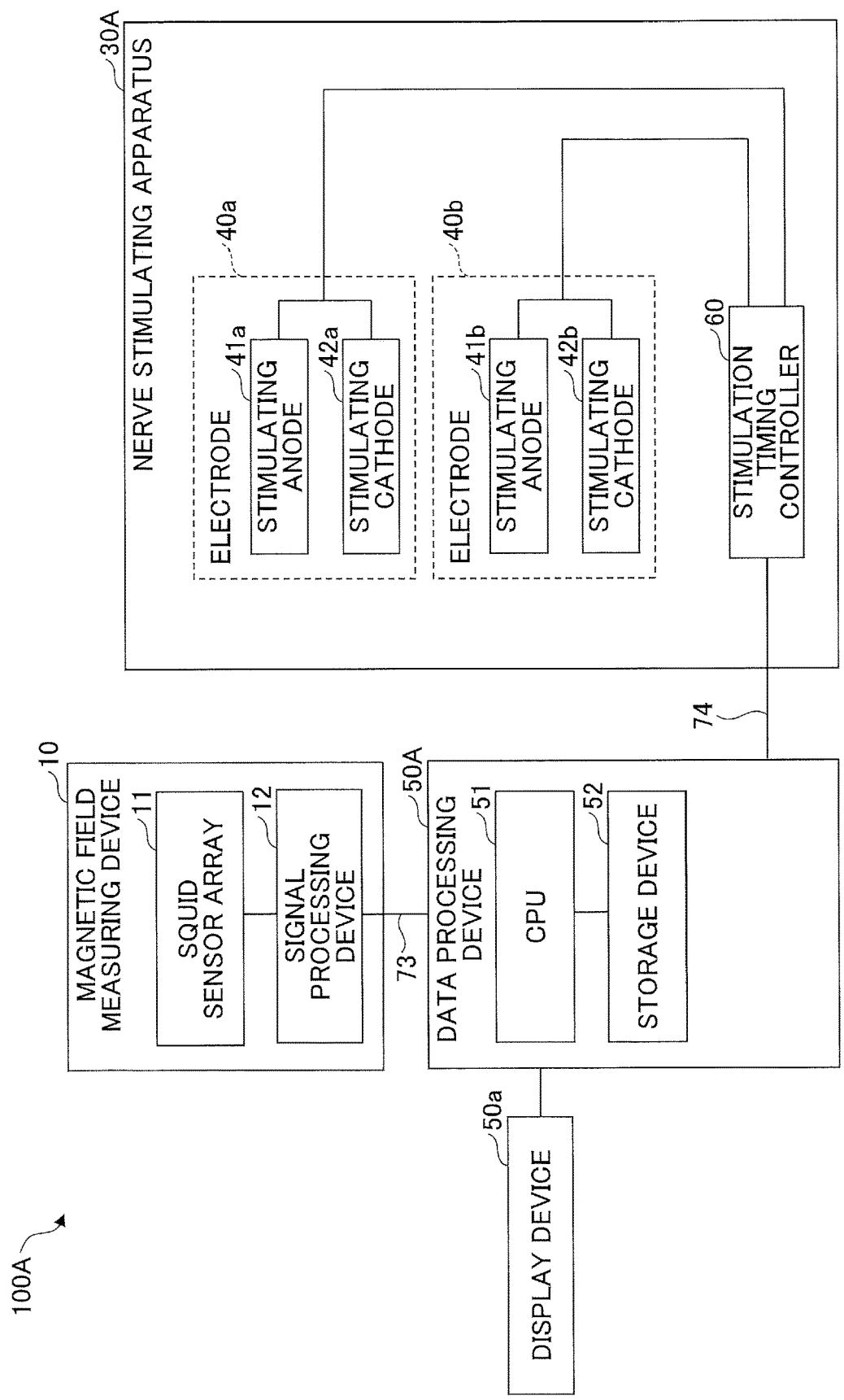
FIG. 10 is a functional block diagram of a biometric information measuring system according to a second embodiment of the present invention.

FIG. 10 is a functional block diagram of a biometric information measuring system according to a second embodiment of the present invention. For elements similar to FIG. 3, the same reference numerals will be used, and the detailed description will be omitted. A biometric information measuring system 100A illustrated in FIG. 10 includes the magnetic field measuring device 10, a nerve stimulating apparatus 30A, a data processing device 50A, and the display device 50a. A system configuration of the biometric information measuring system 100A is similar to the system configuration of FIG. 1 or FIG. 2.

The data processing device 50A has a configuration and function similar to the data processing device 50 except that the stimulation timing controller 60 is removed from the data processing device 50 illustrated in FIG. 3. The nerve stimulating apparatus 30A has a configuration and function similar to the nerve stimulating apparatus 30 except that the stimulation timing controller 60 is added to the nerve stimulating apparatus 30 illustrated in FIG. 3.

A flow of a magnetic field measurement operation performed by the biometric information measuring system 100A is similar to the flow of FIG. 8. In the pre-measurement mode, the latency, which is a feature point of the magnetic field waveform, is calculated using any one of the methods described with reference to FIG. 4, FIG. 6, or FIG. 7. An example of temporal changes in the signal strength is similar to the example in FIG. 9.

As described, in the second embodiment, the magnetic field strength generated by the subject P can be increased, as in the first embodiment described above. Further, in the second embodiment, the stimulation timing controller 60 is included in the nerve stimulating apparatus 30A so that generating timings of generating the electrical stimuli generated from the electrodes 40a and 40b can be set using an existing data processing device 50A.

Third Embodiment

Figure 11:
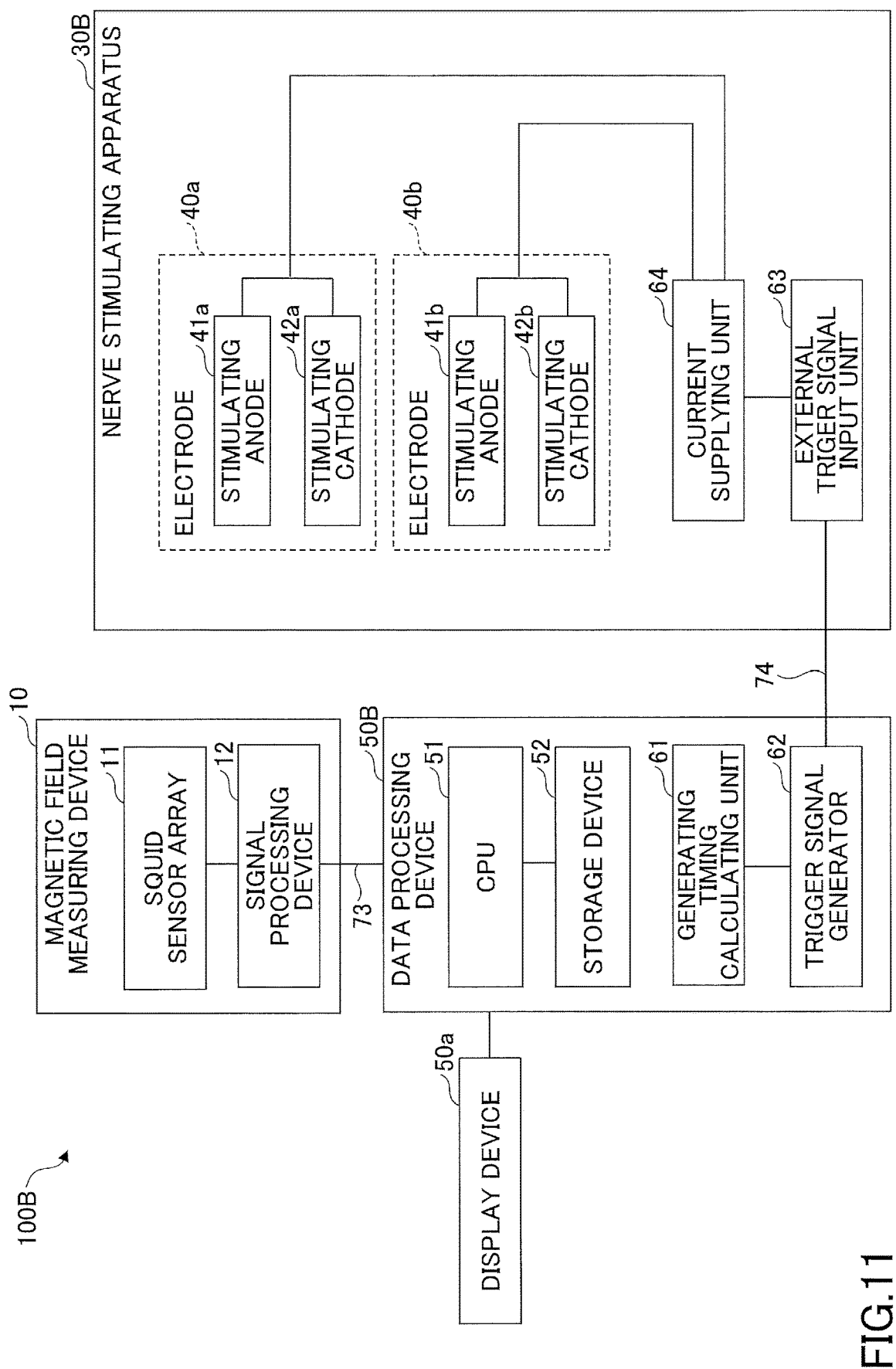
FIG. 11 is a functional block diagram of a biometric information measuring system according to a third embodiment of the present invention.

FIG. 11 is a functional block diagram of a biometric information measuring system according to a third embodiment of the present invention. For elements similar to FIG. 3, the same reference numerals will be used, and the detailed description will be omitted. A biometric information measuring system 100B illustrated in FIG. 11 includes the magnetic field measuring device 10, a nerve stimulating apparatus 30B, a data processing device 50B, and the display device 50a. A system configuration of the biometric information measuring system 100B is similar to the system configuration of FIG. 1 or FIG. 2.

The data processing device 50B has a configuration and function similar to the data processing device 50 except that a generating timing calculating unit 61 and a trigger signal generator 62 are included instead of the stimulation timing controller 60 of the data processing device 50 illustrated in FIG. 3. The nerve stimulating apparatus 30B has a configuration and function similar to the nerve stimulating apparatus 30 except that an external trigger signal input unit 63 and a current supplying unit 64 are added to the nerve stimulating apparatus 30 illustrated in FIG. 3. The generating timing calculating unit 61 and the trigger signal generator 62 are examples of the stimulation timing controller and are examples of the stimulation timing control device.

The generating timing calculating unit 61 operates in the pre-measurement mode and calculates latency until a response (a feature point) from the measurement region is generated in response to the electrical stimuli respectively applied from the electrodes 40a and 40b to the application regions of the subject P. The generating timing calculating unit 61 performs processing similar to the processing of steps S12, S14, and S16 illustrated in FIG. 8. The latency is the peak latency or the rise latency, as described in FIG. 4, 6 or 7. The generating timing calculating unit 61 sets timings of generating the stimuli at the electrodes 40a and 40b so that the feature points of two response waveforms corresponding to the electrodes 40a and 40b appear at the same time. A function of the generating timing calculating unit 61 is similar to the function of the stimulation timing controller 60 described with reference to the function of FIG. 3 excluding the function of generating electrical stimulus to the electrodes 40a and 40b.

For example, a stimulus generating timing calculated by the generating timing calculating unit 61 is stored in the storage device 52. The stimulus generating timing stored in the storage device 52 includes delay electrode information indicating the electrode 40 that delays the generation of the electrical stimulus and delay time information indicating delay time of the electrical stimulus of the other electrode 40 relative to the one electrode 40.

The trigger signal generator 62 is connected to the external trigger signal input unit 63 of the nerve stimulating apparatus 30B through the signal line 74 and outputs a trigger signal to the external trigger signal input unit 63. For example, the trigger signal output by the trigger signal generator 62 includes at least one of application electrode information, delay electrode information, delay time information, or an application start instruction. The application electrode information indicates the electrode 40 that generates the electrical stimulus. For example, the application electrode information indicates one of the electrodes 40a and 40b in the pre-measurement mode and both of the electrodes 40a and 40b in the normal measurement mode. When the application electrode information indicates one of the electrodes 40a and 40b, delay electrode information and delay time information are not used. The application start instruction indicates a start instruction of applying the electrical stimulus (a start instruction of applying the electrical stimulus as an original trigger signal).

In the pre-measurement mode, the trigger signal generator 62 outputs the application electrode information indicating one of the electrodes 40a and 40b as a trigger signal to the external trigger signal input unit 63 before the CPU 51 outputs a measurement start instruction. At this time, the trigger signal generator 62 may output dummy delay electrode information and dummy delay time information to the external trigger signal input unit 63.

In the normal measurement mode, the trigger signal generator 62 outputs the application electrode information, the delay electrode information, and the delay time information stored in the storage device 52 as the trigger signal to the external trigger signal input unit 63 before the CPU 51 outputs the measurement start instruction.

The trigger signal generator 62 outputs the application start instruction as the trigger signal to the external trigger signal input unit 63 based on the measurement start instruction received through an input device (which is not illustrated) connected to the data processing device 50A in the pre-measurement mode and the normal measurement mode. The measurement start instruction is generated by an input device, such as a mouse or a keyboard, being operated by an operator or the like operating the biometric information measuring system 100B.

The external trigger signal input unit 63 decodes the trigger signal received through the signal line 74 and performs an operation according to a decoded result. When receiving the application electrode information, the delay electrode information, or the delay time information, the external trigger signal input unit 63 stores the application electrode information, the delay electrode information, or the delay time information, which is received, in an internal register provided in the nerve stimulating apparatus 30B or the like. When receiving the application start instruction, the external trigger signal input unit 63 outputs a start timing signal indicating a start of an application to the current supplying unit 64.

When receiving the application start instruction in a state in which the application electrode information indicating one of the electrodes 40a and 40b is stored in the internal register, the current supplying unit 64 supplies a predetermined current to only one of the electrodes 40 indicated by the application electrode information to generate the electrical stimulus.

When receiving the application start instruction in a state in which the application electrode information indicating both electrodes 40a and 40b is stored in the internal register, the current supplying unit 64 reads out the delay electrode information and the delay time information from the internal register. The current supplying unit 64 outputs a predetermined current to the electrodes 40a and 40b simultaneously to generate the electrical stimulus when the delay time information indicates "ms".

When the read-out delay time information indicates a value other than "0 ms", the current supplying unit 64 first outputs a predetermined current to one electrode 40 that is not an electrode 40 indicated by the delay electrode information and generates the electrical stimulus. Then, the current supplying unit 64 outputs a predetermined current to the other electrode 40 indicated by the delay electrode information to generate the electrical stimulus after a delay time indicated by the delay time information has passed from when the current supplying unit 64 outputs the predetermined current to the one electrode 40.

The current supplying unit 64 may read out the application electrode information, the delay electrode information, and the delay time information from the internal register in response to receiving the application start instruction. The current supplying unit 64 may read out the application electrode information, the delay electrode information, and the delay time information from the internal register in advance before receiving the application start instruction.

For example, the nerve stimulating apparatus 30B notifies the magnetic field measuring device 10 of the generation of the electrical stimulus in synchronization with the generation of the electrical stimulus from the electrode 40. However, in the normal measurement mode, when the electrical stimuli generated by the two electrodes 40 are not simultaneous, the nerve stimulating apparatus 30B notifies the magnetic field measuring device 10 of the generation of the electrical stimulus in synchronization with the generation of the electrical stimulus from the electrode 40 that generates the electrical stimulus earlier. The nerve stimulating apparatus 30B does not notify the magnetic field measuring device 10 of the generation of the electrical stimulus in synchronization with the generation of the electrical stimulus from the electrode 40 that generates the electrical stimulus later.

The magnetic field measuring device 10 starts measuring the magnetic field by using the SQUID sensor array 11 in response to a notification from the nerve stimulating apparatus 30B and generates magnetic field data by processing the measured magnetic field signal by using the signal processing device 12. Instead of the nerve stimulating apparatus 30B notifying the generation of the electrical stimulus from the electrode 40, the data processing device 50B may notify the magnetic field measuring device 10 of the generation of the electrical stimulus from the electrode 40 in response to the application start instruction.

Instead of using delay electrode information, the delay time information indicating the delay time of each of the electrodes 40a and 40b relative to a reference timing may be used. In this case, in the pre-measurement mode, the delay time of the electrode 40a and the delay time of the electrode 40b indicated by the delay time information are both set to "0 ms". The current supplying unit 64 causes the electrode 40 indicated by the application electrode information to generate the electrical stimulus in response to the application start instruction.

In the normal measurement mode, in the delay time information, the delay time of one electrode 40 is set to "0 ms" and the delay time of the other electrode 40 is set to a value indicating delay time of the electrical stimulus of the other electrode 40 relative to the one electrode 40.

The above operation enables the nerve stimulating apparatus 30B to generate the electrical stimuli at the electrodes 40a and 40b in response to the application start instruction from the trigger signal generator 62 without recognizing the pre-measurement mode and the normal measurement mode. Thus, for the nerve stimulating apparatus 30B, a commercial product (i.e., a general purpose product) can be used. A flow of a magnetic field measurement operation performed by the biometric information measuring system 100B is similar to the flow of FIG. 8. The generating timing calculating unit 61 and the trigger signal generator 62 may be disposed in the signal processing device 12 of the magnetic field measuring device 10 instead of the data processing device 50B. An example of temporal changes in the signal strength is similar to the example in FIG. 9.

As described, the magnetic field strength generated by the subject P can be increased in the third embodiment as in the first embodiment described above. In the third embodiment, the external trigger signal input unit 63 can cause the current supplying unit 64 to output an electrical current to the electrode 40 in response to the trigger signal generated by the trigger signal generator 62. This enables the nerve stimulating apparatus 30B to generate the electrical stimulus at the electrode 40 in response to the trigger signal output from the trigger signal generator 62 without recognizing the pre-measurement mode and the normal measurement mode. Thus, for example, a commercially available nerve stimulating apparatus 30B can be used to reduce the cost of the biometric information measuring system 100B.

Fourth Embodiment

Figure 12:
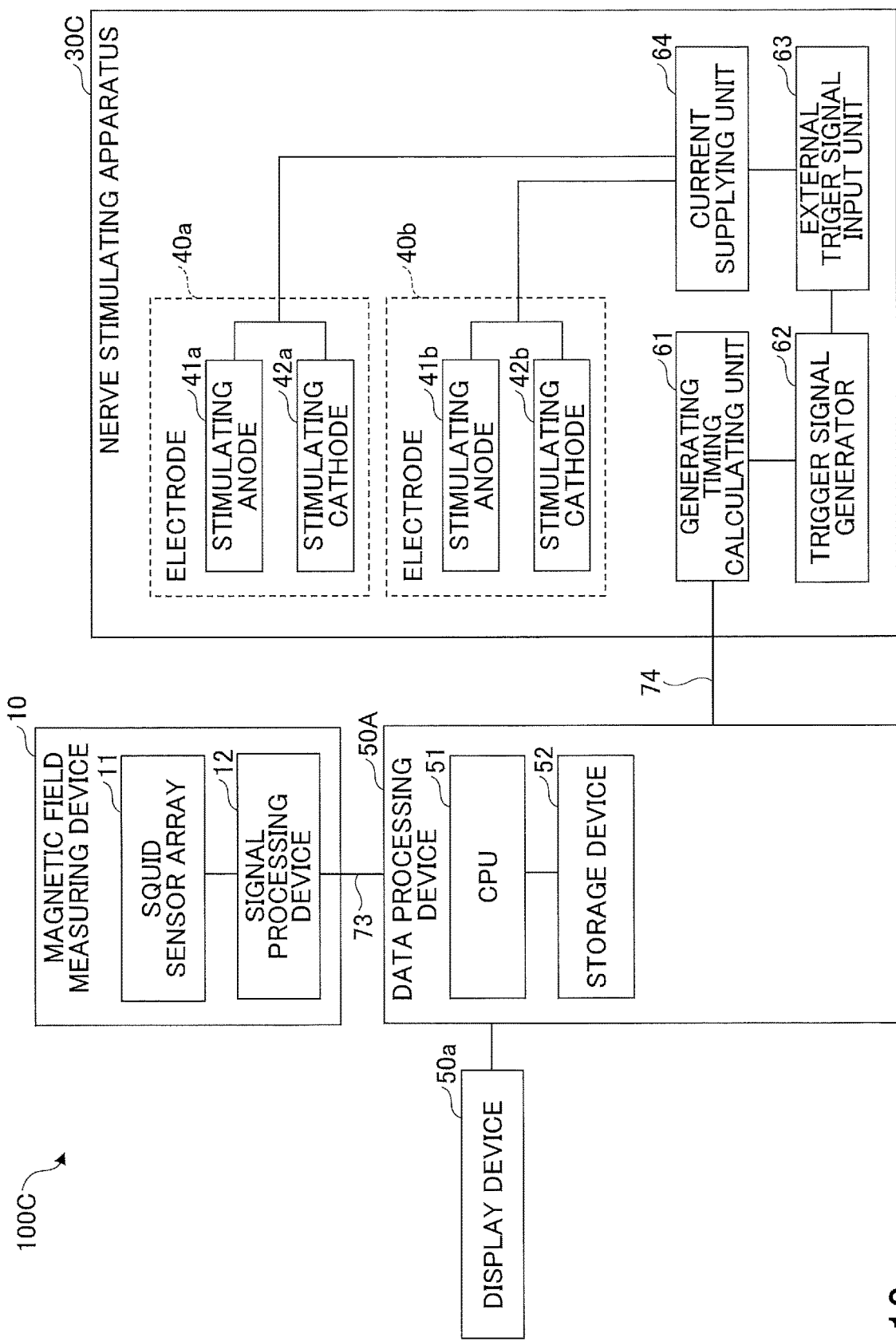
FIG. 12 is a functional block diagram of a biometric information measuring system according to a fourth embodiment of the present invention.

FIG. 12 is a functional block diagram of a biometric information measuring system according to a fourth embodiment of the present invention. For elements similar to the elements of FIGS. 3, 10, and 11, the same reference numerals will be used and the detailed description will be omitted. A biometric information measuring system 100C illustrated in FIG. 12 includes the magnetic field measuring device 10, a nerve stimulating apparatus 30C, the data processing device 50A, and the display device 50a. A system configuration of the biometric information measuring system 100C is similar to the system configuration of FIG. 1 or FIG. 2.

The nerve stimulating apparatus 30C has a configuration and function similar to the configuration and function of the nerve stimulating apparatus 30B, except that the generating timing calculating unit 61 and the trigger signal generator 62 are added to the nerve stimulating apparatus 30B illustrated in FIG. 11. That is, in the present embodiment, the existing data processing device 50A can be used to perform the operation of the pre-measurement mode and the operation of the normal measurement mode using the stimulus generating timing that has been set in the pre-measurement mode.

In the pre-measurement mode, the CPU 51 outputs an instruction to simultaneously generate the electrical stimuli at the electrodes 40a and 40b to the trigger signal generator 62 through the generating timing calculating unit 61 of the nerve stimulating apparatus 30C. When the measurement of the magnetic field in the pre-measurement mode is completed, the CPU 51 causes the generating timing calculating unit 61 of the nerve stimulating apparatus 30C to calculate the stimulus generating timings of the electrodes 40a and 40b used in the normal measurement mode.

A function of the generating timing calculating unit 61 is similar to the function of the generating timing calculating unit 61 described with reference to FIG. 11. However, the generating timing calculating unit 61 of the present embodiment has a function to read the magnetic field data measured in the pre-measurement mode from the storage device 52 and a function to store the calculated stimulus generating timing in the storage device 52. The calculated stimulus generating timing may be stored in a register or a memory, which are not illustrated, provided in the nerve stimulating apparatus 30C.

Functions of the trigger signal generator 62, the external trigger signal input unit 63, and the current supplying unit 64 are similar to the functions of the trigger signal generator 62, the external trigger signal input unit 63, and the current supplying unit 64 illustrated in FIG. 11, respectively. However, the trigger signal generator 62 outputs the trigger signal to the external trigger signal input unit 63 in response to the measurement start instruction from the CPU 51 received through the signal line 74.

A flow of the magnetic field measurement operation performed by the biometric information measuring system 100C is similar to the flow of FIG. 8. In the pre-measurement mode, the latency, which is the feature point of the magnetic field waveform, is calculated using any one of the methods illustrated in FIG. 4, FIG. 6, and FIG. 7. An example of temporal changes in the signal strength is similar to the example in FIG. 9.

As described, in the fourth embodiment, the magnetic field strength generated by the subject P can be increased as in the above-described embodiments. Further, in the fourth embodiment, the existing data processing device 50A can be used to perform the operation of the pre-measurement mode and the operation of the normal measurement mode using the stimulus generating timings set in the pre-measurement mode.

Fifth Embodiment

Figure 13:
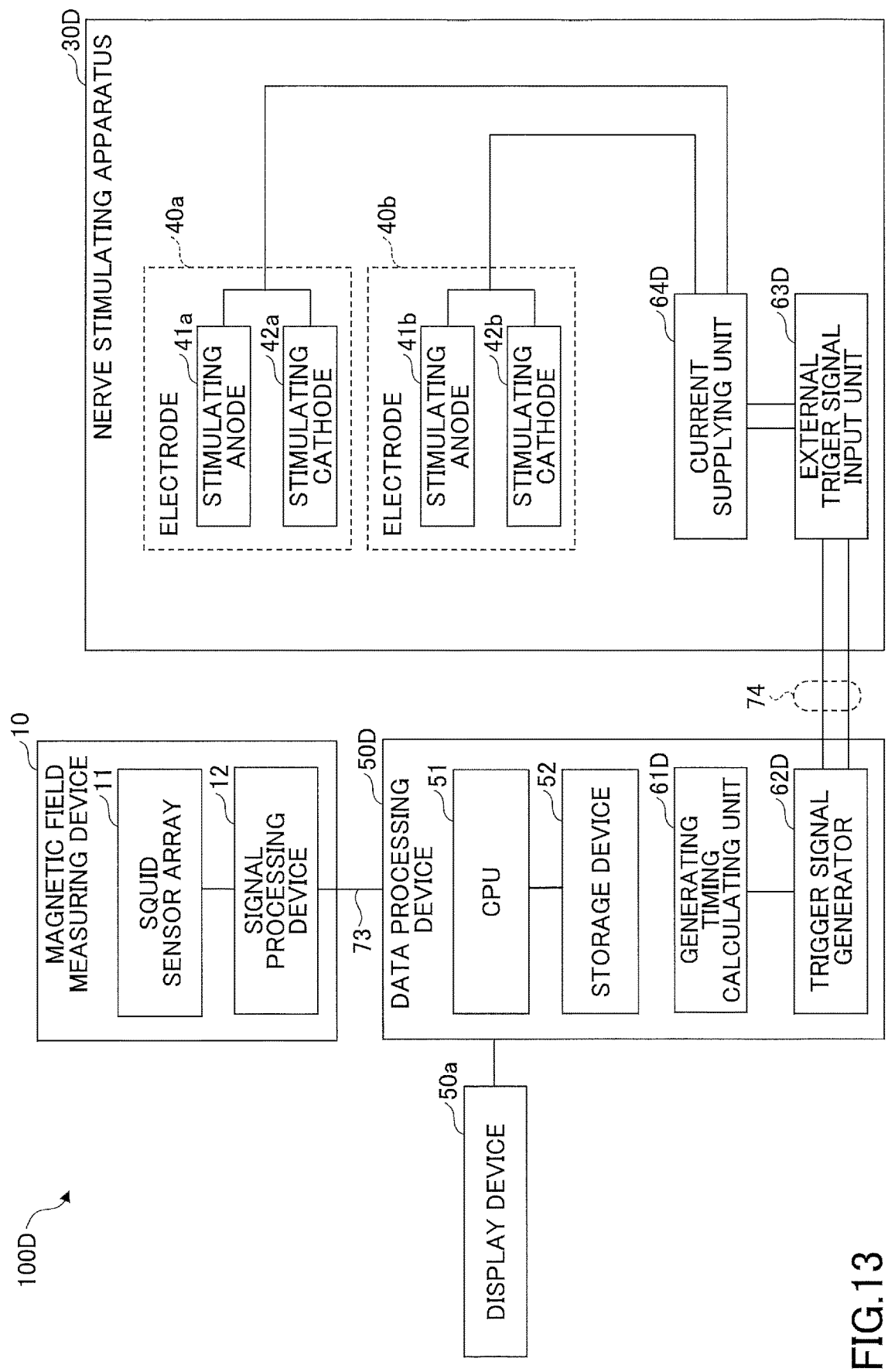
FIG. 13 is a functional block diagram of a biometric information measuring system according to a fifth embodiment of the present invention.

FIG. 13 is a functional block diagram of a biometric information measuring system according to a fifth embodiment of the present invention. For elements similar to the above-described embodiments, the same reference numerals will be used and the detailed description will be omitted. A biometric information measuring system 100D illustrated in FIG. 13 includes the magnetic field measuring device 10, a nerve stimulating apparatus 30D, a data processing device 50D, and the display device 50a. A system configuration of the biometric information measuring system 100D is similar to the system configuration of FIG. 1 or FIG. 2.

The data processing device 50D includes a generating timing calculating unit 61D and a trigger signal generator 62D instead of the generating timing calculating unit 61 and the trigger signal generator 62 of the data processing device 50B illustrated in FIG. 11. Other components and functions of the data processing device 50D are similar to the components and functions of the data processing device 50B. The generating timing calculating unit 61D and the trigger signal generator 62D are examples of the stimulation timing control device.

The nerve stimulating apparatus 30D has a configuration and function similar to the configuration and function of the nerve stimulating apparatus 30B except that the external trigger signal input unit 63D and the current supplying unit 64D are included instead of the external trigger signal input unit 63 and the current supplying unit 64 of the nerve stimulating apparatus 30B illustrated in FIG. 11. The trigger signal generator 62D and the external trigger signal input unit 63D are connected through signal lines 74 corresponding to the electrodes 40a and 40b respectively. The external trigger signal input unit 63D and the current supplying unit 64D are connected through signal lines corresponding to the electrodes 40a and 40b respectively.

The generating timing calculating unit 61D, in the pre-measurement mode, calculates the stimulus generating timings of the electrodes 40a and 40b so that the feature points of two response waveforms corresponding to the electrodes 40a and 40b appear at the same time. In the generating timing calculating unit 61D, an operation performed until the stimulus generating timings of the electrodes 40a and 40b are calculated is similar to the operation of the generating timing calculating unit 61 described with reference to FIG. 11. The generating timing calculating unit 61D stores the calculated stimulus generating timings of the electrodes 40a and 40b in the storage device 52.

In the pre-measurement mode, the trigger signal generator 62D successively generates a trigger signal that generates the electrical stimulus at each of the electrodes 40a and 40b, and successively outputs the generated trigger signal to the nerve stimulating apparatus 30D by using the signal lines 74 that are different from each other. By using the signal line 74 dedicated for each of the electrodes 40a and 40b, the trigger signal generator 62D does not need to generate a trigger signal identifying the electrodes 40a and 40b.

The trigger signal generator 62D outputs a pair of trigger signals to generate the electrical stimuli at the electrodes 40a and 40b to the external trigger signal input unit 63D in the normal measurement mode according to the stimulus generating timings of the electrodes 40a and 40b stored in the storage device 52.

When receiving the trigger signal through the signal line 74 corresponding to the electrode 40a, the external trigger signal input unit 63D outputs the start timing signal indicating the application start to the current supplying unit 64D through the signal line corresponding to the electrode 40a. When receiving the trigger signal through the signal line 74 corresponding to electrode 40b, the external trigger signal input unit 63D outputs the start timing signal indicating the application start to the current supplying unit 64D through the signal line corresponding to electrode 40b.

The current supplying unit 64D supplies a predetermined current to the electrode 40 corresponding to the signal line through which the start timing signal is received to generate the electrical stimulus. This enables the trigger signal generator 62D, the external trigger signal input unit 63D, and the current supplying unit 64D to generate the electrical stimuli at the electrodes 40a and 40b without using the application electrode information, the delay electrode information, and the delay time information. In other words, by outputting only a trigger signal indicating the application start instruction from the trigger signal generator 62D to the external trigger signal input unit 63D, the electrical stimuli can be generated at the electrodes 40a and 40b.

For the nerve stimulating apparatus 30D, a commercial product (i.e., a general purpose product) can be used because the nerve stimulating apparatus 30D operates in response to the trigger signal indicating the application start indication. The generating timing calculating unit 61D and the trigger signal generator 62D may be disposed in the signal processing device 12 of the magnetic field measuring device 10 instead of the data processing device 50D.

As described, in the fifth embodiment, the magnetic field strength generated by the subject P can be increased as in the above-described embodiments. Further, in the fifth embodiment, the nerve stimulating apparatus 30D can generate the electrical stimulus at each of the electrodes 40a and 40b in response to a corresponding one of the trigger signals of the electrodes 40a and 40b output by the trigger signal generator 62D. This enables, for example, the commercially available nerve stimulating apparatus 30D to be used to reduce the cost of the biometric information measuring system 100D.

Sixth Embodiment

Figure 14:
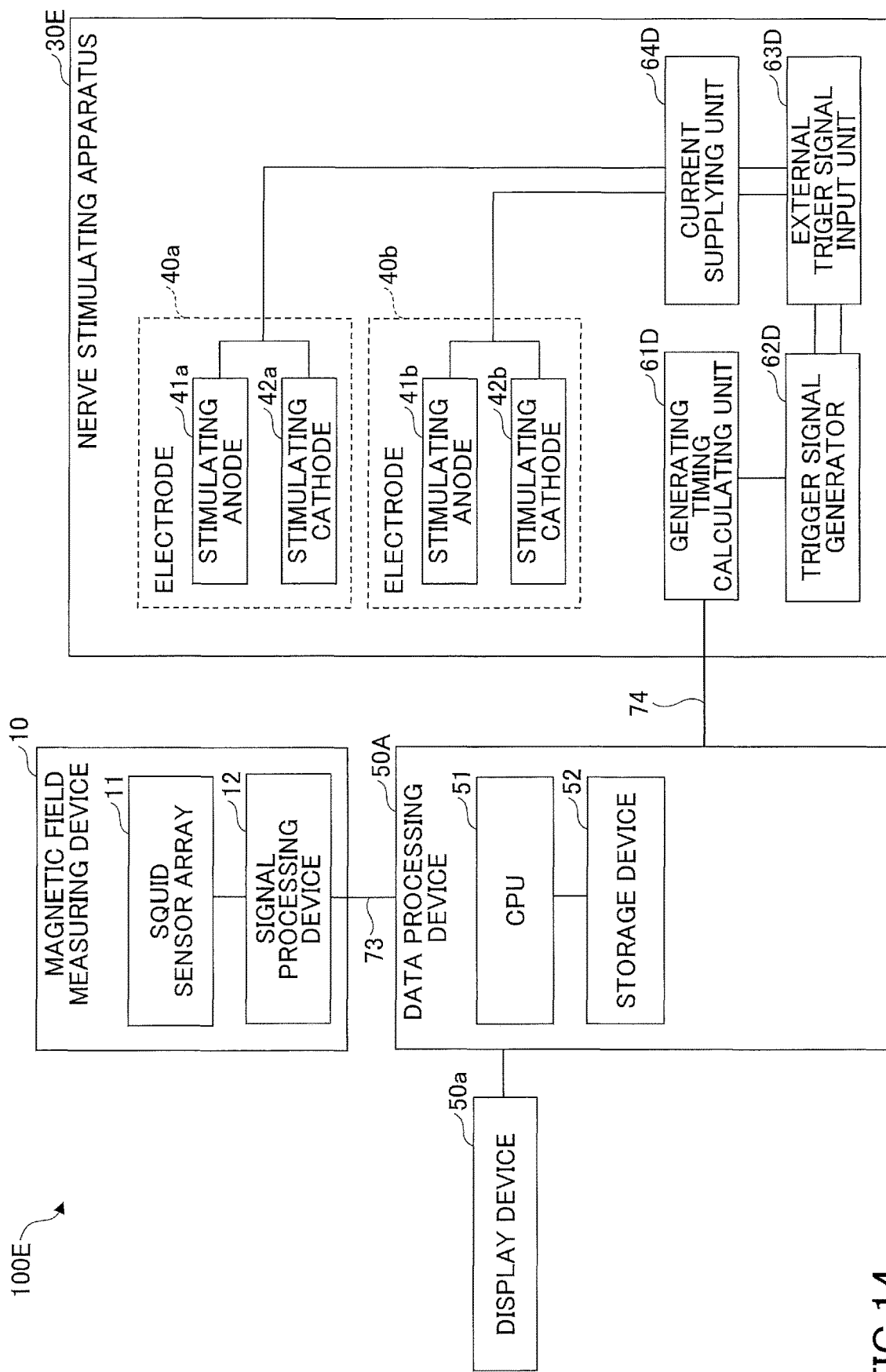
FIG. 14 is a functional block diagram of a biometric information measuring system according to a sixth embodiment of the present invention.

FIG. 14 is a functional block diagram of a biometric information measuring system according to a sixth embodiment of the present invention. For elements similar to the above-described embodiments, the same reference numerals will be used and the detailed description will be omitted. A biometric information measuring system 100E illustrated in FIG. 14 includes the magnetic field measuring device 10, a nerve stimulating apparatus 30E, the data processing device 50A, and the display device 50a. A system configuration of the biometric information measuring system 100E is similar to the system configuration of FIG. 1 or FIG. 2.

The nerve stimulating apparatus 30E has a configuration and function similar to the configuration and function of the nerve stimulating apparatus 30D, except that the generating timing calculating unit 61D and the trigger signal generator 62D are added to the nerve stimulating apparatus 30D illustrated in FIG. 13. That is, in the present embodiment, the existing data processing device 50A can be used to perform the operation of the pre-measurement mode and the operation of the normal measurement mode using the stimulus generating timings set in the pre-measurement mode.

A function of the generating timing calculating unit 61D is similar to the function of the generating timing calculating unit 61D described with reference to FIG. 13. However, the generating timing calculating unit 61D of the present embodiment has a function to read the magnetic field data measured in the pre-measurement mode from the storage device 52 and a function to store the calculated stimulus generating timing in the storage device 52. The calculated stimulus generating timing may be stored in a register or a memory, which are not illustrated, provided in the nerve stimulating apparatus 30E.

Functions of the trigger signal generator 62D, the external trigger signal input unit 63D, and the current supplying unit 64D are similar to the functions of the trigger signal generator 62D, the external trigger signal input unit 63D, and the current supplying unit 64D illustrated in FIG. 13 respectively. However, the trigger signal generator 62D outputs the trigger signal to the external trigger signal input unit 63D in response to the measurement start instruction received from the CPU 51 through the signal line 74.

A flow of a magnetic field measurement operation performed by the biometric information measuring system 100E is similar to the flow of FIG. 8. In the pre-measurement mode, the latency, which is the feature point of the magnetic field waveform, is calculated using any one of the methods illustrated in FIG. 4, FIG. 6, and FIG. 7. An example of temporal changes in the signal strength is similar to the example in FIG. 9.

As described, in the sixth embodiment, the magnetic field strength generated by the subject P can be increased as in the above-described embodiments. As in the fourth embodiment, the existing data processing device 50A can be used to perform the operation of the pre-measurement mode and the operation of the normal measurement mode using the stimulus generating timings set in the pre-measurement mode.

Seventh Embodiment

Figure 15:
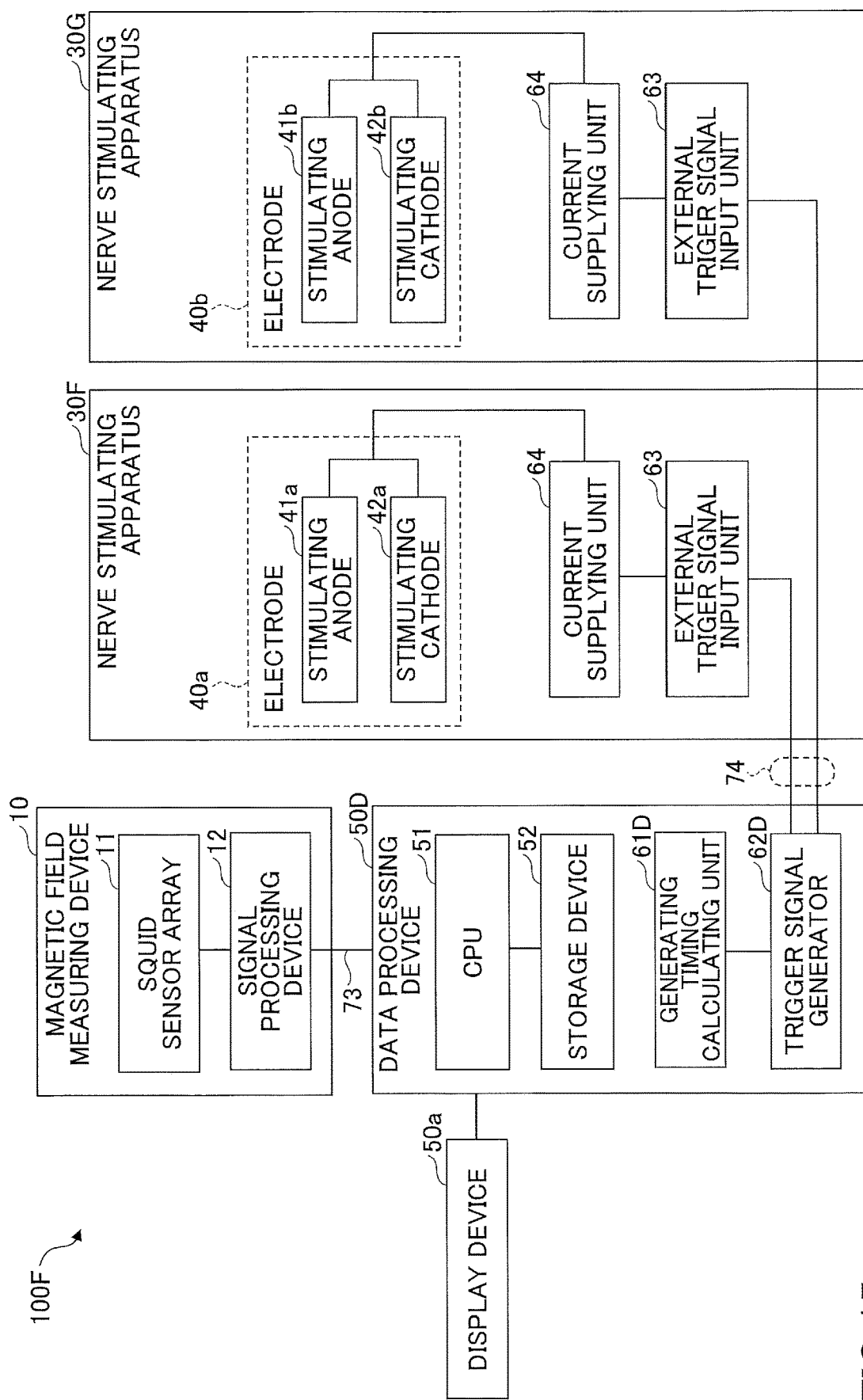
FIG. 15 is a functional block diagram of a biometric information measuring system according to a seventh embodiment of the present invention.

FIG. 15 is a functional block diagram of a biometric information measuring system according to a seventh embodiment of the present invention. For elements similar to the above-described embodiments, the same reference numerals will be used and the detailed description will be omitted. A biometric information measuring system 100F illustrated in FIG. 15 includes the magnetic field measuring device 10, two nerve stimulating apparatuses 30F and 30G, the data processing device 50D, and the display device 50a. A system configuration of the biometric information measuring system 100F is similar to the system configuration of FIG. 1 or FIG. 2.

The nerve stimulating apparatus 30F includes the external trigger signal input unit 63, the current supplying unit 64, and the electrode 40a. The nerve stimulating apparatus 30G includes the external trigger signal input unit 63, the current supplying unit 64, and the electrode 40b. The nerve stimulating apparatuses 30F and 30G are examples of a sub-stimulator, and two sub-stimulators constitute a nerve stimulating apparatus in the present embodiment.

In the pre-measurement mode, the trigger signal generator 62D successively generates a trigger signal that generates the electrical stimulus at each of the electrodes 40a and 40b and successively outputs the generated trigger signal to the external trigger signal input unit 63 of each of the nerve stimulating apparatuses 30F and 30G. Thus, the trigger signal generator 62D is connected to the external trigger signal input unit 63 of the nerve stimulating apparatuses 30F and 30G through the respective signal lines 74 different from each other.

Each of the external trigger signal input units 63 of the nerve stimulating apparatus 30F and 30G outputs the start timing signal indicating the application start to the corresponding current supplying unit 64 in response to the trigger signal received from the trigger signal generator 62D. The nerve stimulating apparatuses 30F and 30G independently generate the electrical stimuli at the electrodes 40a and 40b. For example, for the nerve stimulating apparatuses 30F and 30G, commercial products (i.e., general purpose products) may be used.

A flow of a magnetic field measurement operation performed by the biometric information measuring system 100F is similar to the flow of FIG. 8. In the pre-measurement mode, the latency, which is the feature point of the magnetic field waveform, is calculated using any one of the methods illustrated in FIG. 4, FIG. 6, and FIG. 7. An example of temporal changes in the signal strength is similar to the example in FIG. 9.

As described, in the seventh embodiment, the magnetic field strength generated by the subject P can be increased as in the above-described embodiments. In addition, as in the fifth embodiment, each of the nerve stimulating apparatuses 30F and 30G can generate the electrical stimulus at the corresponding electrode 40 (i.e., 40a or 40b) in response to the trigger signal output by the trigger signal generator 62D for each of the electrodes 40a and 40b. This enables, for example, the commercially available nerve stimulating apparatuses 30F and 30G having one channel (i.e., only one electrode 40) to be used to reduce the cost of the biometric information measuring system 100F.

In the embodiments described above, examples in which the nerve stimulating apparatuses 30, 30A, 30B, 30C, 30D, 30E, 30F, and 30G generate the electrical stimuli (i.e., the current pulses) from the electrodes 40a and 40b have been described. However, the nerve stimulating apparatuses 30, 30A, 30B, 30D, 30E, 30F, and 30G may generate magnetic stimuli, acoustic stimuli, or mechanical stimuli, and may include needle-like electrodes 40 inserted into the skin. In this case, the stimulus generating timings can be set in the pre-measurement mode so that response timings, at a particular nerve region, such as the spinal cord, with respect to the stimuli match.

In the above-described embodiment, an example in which the timing of generating the stimulus is adjusted so that the response timings, at a particular nerve region, such as the spinal cord, with respect to the electrical stimuli generated from the two electrodes 40a and 40b match, to measure the magnetic field has been described. However, stimulus generating timings may be adjusted so that response timings at the spinal cord with respect to the electrical stimuli generated from three or more electrodes 40 match, and three or more responses may be overlapped. Three or more stimuli may be magnetic, acoustic, or mechanical.

Further, in the embodiments described above, an example in which the electrical stimuli are applied to the popliteal regions of the both legs or the left and right elbows to measure the magnetic field generated from a particular nerve region, such as the spinal cord, has been described. However, for example, the stimuli may be applied to the index and middle fingers of the left or right hand to measure the magnetic field generated by the median nerve of the palm or the arm corresponding to the fingers to which the stimuli have been applied. The stimuli may be applied to three or more fingers or to at least one finger of the left and right hands.

In the above-described embodiments, a process of calculating the latency in the pre-measurement mode has been described with an example using the magnetic field measurement data obtained in response to the electrical stimulus. However, the latency may be calculated using not only the magnetic field measurement data, but also current data estimated (i.e., reconstructed) based on the magnetic field measurement data. That is, application timings of the electrical stimuli generated by two electrodes 40a and 40b may be adjusted using latency calculated from the current data.

Figure 16:
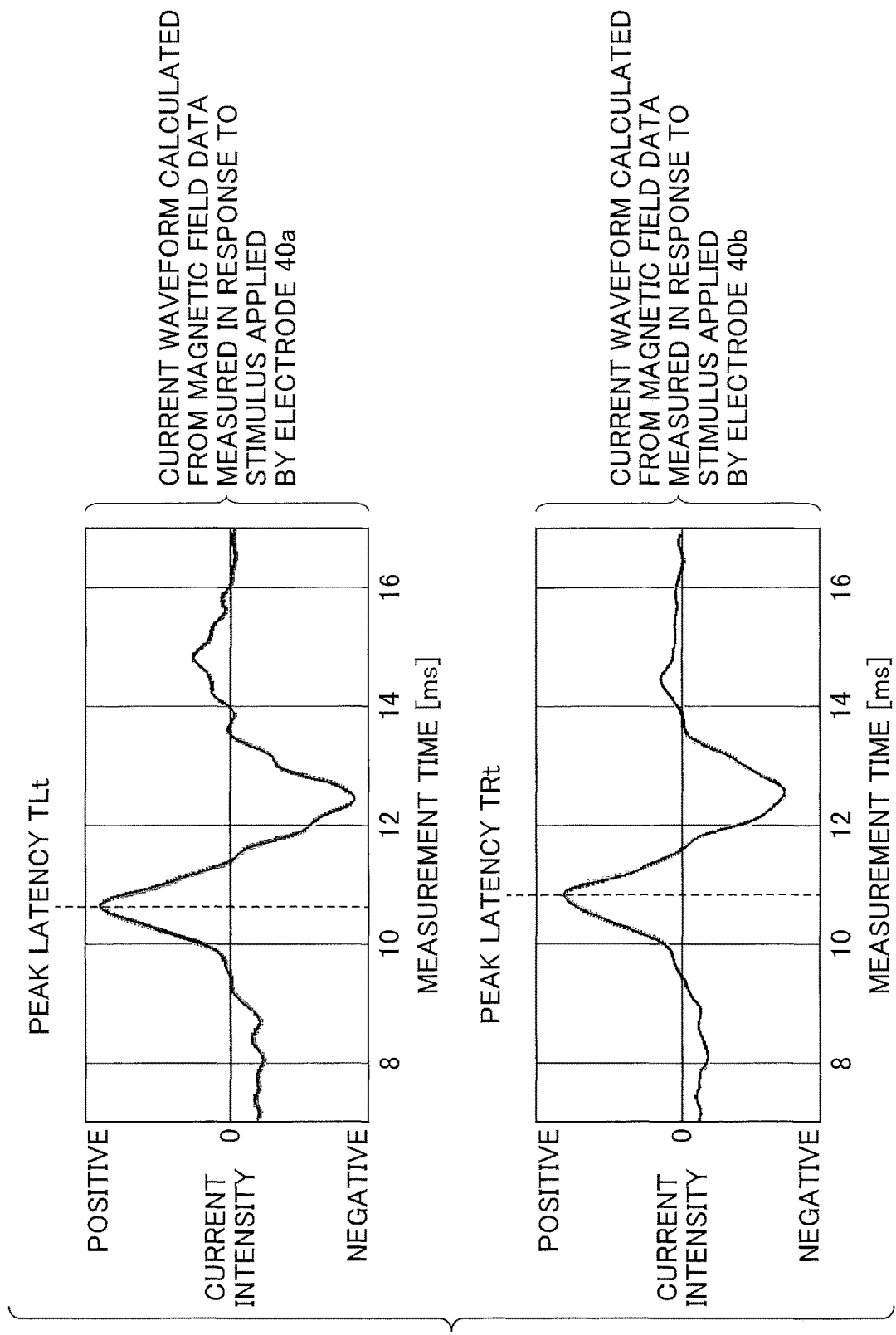
FIG. 16 is an explanatory drawing illustrating an example of calculating latency by using current data estimated based on magnetic field measurement data in the pre-measurement mode of the biometric information measuring system.

FIG. 16 illustrates an example of calculating latency by using current data estimated based on the magnetic field measurement data in the pre-measurement mode of the biometric information measuring system described above. For example, current intensity waveforms illustrated in FIG. 16 are results of calculating current distribution waveforms of the nerve electrical activities at a position between the L2 vertebral body and the L3 vertebral body (i.e., the intervertebral space) based on the neural activities of the sciatic nerves caused by electrical stimuli from the left and right legs. The peak latency, which is peak time of the current waveform, may be the feature amount.

The magnetic field is a component waveform of X, Y, or Z (i.e., a direction in three dimensions), and, for example, if an SN ratio on the X-axis was poor, it would be difficult to detect a temporal feature amount. With respect to this, the current data is calculated by performing estimation (i.e., current reconstruction) based on the three components of X, Y, and Z, and it is possible to obtain a waveform having a good SN ratio, and it is advantageous to adjust the timings more accurately.

Eighth Embodiment

Further, in the above-described embodiments, the process of calculating the latency in the pre-measurement mode has been described with an example in which the magnetic field measurement data is used, but the latency may be calculated not only by using the magnetic field measurement data but also by using electric potential measurement data. For example, in adjusting the timings of applying the electrical stimuli when measuring the neuromagnetic field at the spinal cord of the thoracic spine, an electric potential measuring device may be used to obtain a feature point of an electric potential waveform obtained at the L3 vertebral body (i.e., the thoracic spine) before measuring the neuromagnetic field.

Figure 17:
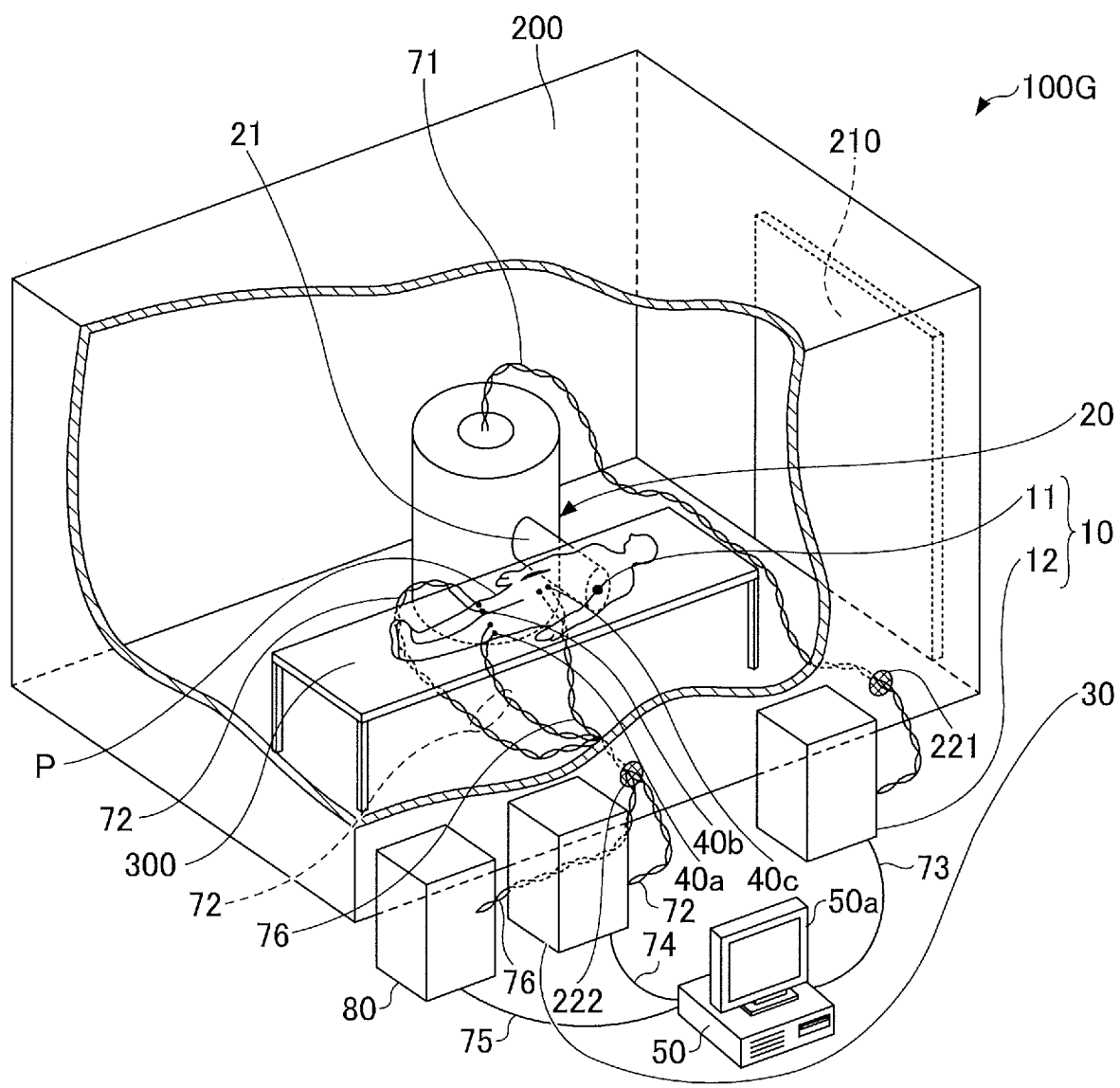
FIG. 17 is a system configuration diagram illustrating an example of a biometric information measuring system according to an eighth embodiment of the present invention.

FIG. 17 is a system configuration diagram illustrating an example of a biometric information measuring system according to an eighth embodiment of the present invention. In a biometric information measuring system 100G illustrated in FIG. 17, the timings of the electrical stimuli applied from the nerve stimulating apparatus 30 are adjusted using a feature point of an electric potential waveform measured in the pre-measurement mode. For elements similar to FIG. 1, the same reference numerals will be used and the detailed description will be omitted. In the biometric information measuring system 100G, an electric potential measuring device 80 that can measure the electric potential difference at the particular region of the living body is added to the configuration of FIG. 1 as a biometric information measuring apparatus in addition to the magnetic field measuring device 10.

In the example illustrated in FIG. 17, electrodes 40c (i.e., recording electrodes for recording the electric potential (a pair of anode and cathode)) of the electric potential measuring device 80 are attached to the skin of the lumbar spine of the subject P (e.g., the L3 vertebral body), and the sciatic nerves of the legs of the subject P are excited by the electrical stimuli applied at the electrodes 40a and 40b attached to the popliteal region of both legs, for example. As a result, the electrical stimuli of the electrodes 40a and 40b transmit the nerve activity of the subject P to the central nerve, and an electric potential waveform based on the nerve activity is measured between the electrodes 40c of the electric potential measuring device 80 for detecting the electric potential. Electric potential measurement data is stored in the electric potential measuring device 80 and is used. More preferably, the electric potential measurement data is transferred to the data processing device 50 through the signal line 75, and the data processing device 50 calculates a feature amount to calculate electrical stimulus timings from the electrodes 40*a* and 40*b*. A twisted cable is preferably used for the signal line 76 connecting the electric potential measuring device 80 and the electrodes 40*c* in order to reduce noise.

Figure 18:
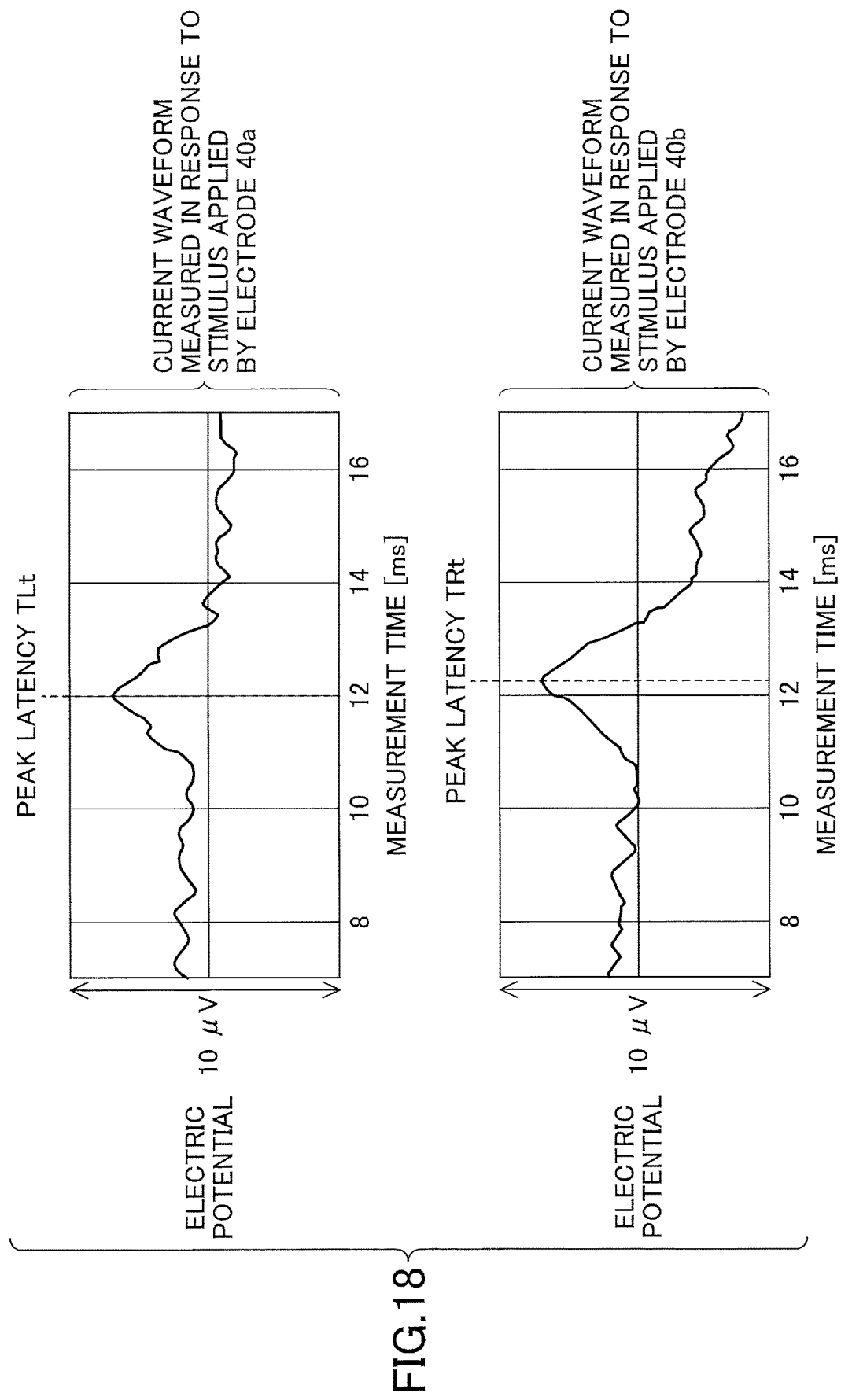
FIG. 18 is an explanatory drawing illustrating an example of calculating latency by using electric potential measurement data in the pre-measurement mode of the biometric information measuring system in FIG. 17.

FIG. 18 illustrates an example of calculating latency by using electric potential measurement data in the pre-measurement mode of the biometric information measuring system 100G of FIG. 17. For example, electric potential waveforms illustrated in FIG. 18 are results of calculating electric potential waveforms of nerve electrical activities at the L3 vertebral body based on nerve activities of the left and right sciatic nerves caused by the electrical stimuli from the left and right legs. Thus, the peak latency TLt and the peak latency TRt, which are the peak time of the electric potential waveforms, may be used as feature amounts. For calculating the feature amounts, an averaging process and a peak latency calculation are performed by the electric potential measuring device 80 or the data processing device 50. In FIG. 17, the electric potential measuring device 80 and the nerve stimulating apparatus 30 have been described as separate devices. However, the embodiment is not limited to this. For example, instead of the electric potential measuring device 80 and the nerve stimulating apparatus 30, a device that can perform both the nerve stimulation and the electric potential measurement may be used.

As described above, in a method of adjusting the application timing of the electrical stimulus when measuring the neuromagnetic field by using the electric potential measuring device 80, for example, when measuring the magnetic field at the lumber spine by using the magnetic field measuring device 10 as the pre-measurement for measuring the magnetic field at the thoracic spine, the subject P needs to move in a longitudinal direction of the table 300 (or a position of the SQUID sensor array 11 (the protrusion 21) needs to be changed with respect to the subject P). However, when the electric potential measuring device 80 is used, the subject P does not need to move (or a position of the SQUID sensor array 11 does not need to be changed), so that the pre-measurement can be performed more easily.

Although the invention has been described above in accordance with the embodiments, the invention is not limited to the requirements described in the embodiments. In these points, alterations can be made without departing from the spirit and scope of the invention, and can be suitably determined according to its application.

What is claimed is:

1. A nerve stimulating apparatus comprising:
   a plurality of stimulating units configured to respectively apply stimuli to a plurality of nerve regions branching from a particular nerve region of a living body, the stimuli being electrical stimuli, magnetic stimuli, acoustic stimuli, or mechanical stimuli; and
   a stimulation timing controller configured to set generating timings of respectively generating the stimuli at the plurality of stimulating units,
   wherein the stimulation timing controller sets the generating timings of generating the stimuli at the plurality of stimulating units based on response results of the particular nerve region, the response results being obtained in response to the stimuli that are respectively generated at the plurality of stimulating units and that are respectively applied to the plurality of nerve regions, and each of the response results being a magnetic field measured by a biomagnetic field measuring device,
   wherein the stimulation timing controller respectively calculates a plurality of latencies each indicating a duration from when a respective one of the stimuli is applied to the living body to when a corresponding one of feature points appears in a response of the living body, for the plurality of stimulating units, based on current data estimated based on the measured magnetic field, and sets the generating timings based on the plurality of calculated latencies.

2. The nerve stimulating apparatus as claimed in claim 1, wherein the stimulation timing controller sets the generating timings based on the plurality of calculated latencies so as to cause the feature points to appear at the same time.

3. The nerve stimulating apparatus as claimed in claim 2, wherein the stimulation timing controller calculates a peak value of a waveform indicating temporal changes of a strength of the response measured by the biomagnetic field measuring device or a rise of the waveform, as each of the feature points.

4. The nerve stimulating apparatus as claimed in claim 2,
   wherein the stimulation timing controller is further configured to calculate the generating timings to cause the feature points to appear at the same time based on the plurality of latencies respectively calculated for the plurality of stimulating units, and a trigger signal generator configured to generate a trigger signal based on the calculated generating timings, and
   wherein the plurality of stimulating units generates the stimuli in response to the trigger signal.

5. The nerve stimulating apparatus as claimed in claim 4,
   wherein the trigger signal generator generates a plurality of said trigger signals respectively output to the plurality of stimulating units, and
   wherein the plurality of stimulating units respectively generates the stimuli in response to the plurality of trigger signals.

6. A biometric information measuring system comprising:
   a nerve stimulating apparatus including a plurality of stimulating units configured to respectively apply stimuli to a plurality of nerve regions branching from a particular nerve region of a living body, the stimuli being electrical stimuli, magnetic stimuli, acoustic stimuli, or mechanical stimuli;
   a biomagnetic field measuring device configured to measure response results of the particular nerve region as biometric information, the response results being generated in response to the stimuli respectively applied to the plurality of nerve regions; and
   a stimulation timing control device configured to set generating timings of respectively generating the stimuli at the plurality of stimulating units,
   wherein the stimulation timing control device sets the generating timings of generating the stimuli at the plurality of stimulating units based on the response results of the particular nerve region, the response results being obtained in response to the stimuli that are respectively generated at the plurality of stimulating units and that are respectively applied to the plurality of nerve regions, and each of the response results being a magnetic field measured by the biomagnetic field measuring device, wherein the stimulation timing controller respectively calculates a plurality of latencies each indicating a duration from when a respective one of the stimuli is applied to the living body to when a corresponding one of feature points appears in a response of the living body, for the plurality of stimulating units, based on current data estimated based on the measured magnetic field, and sets the generating timings based on the plurality of calculated latencies.

7. The biometric information measuring system as claimed in claim 6,
wherein the stimulation timing control device respectively calculates a plurality of latencies each indicating a duration from when a respective one of the stimuli is applied to the living body to when a corresponding one of feature points appears in a response of the living body, for the plurality of stimulating units, based on the response results of the particular nerve region, and sets the generating timings based on the plurality of calculated latencies so as to cause the feature points to appear at the same time.

8. The biometric information measuring system as claimed in claim 7, wherein the stimulation timing control device calculates a peak value of a waveform indicating temporal changes of a strength of the response measured by the biomagnetic field measuring device or a rise of the waveform, as each of the feature points.

9. The biometric information measuring system as claimed in claim 7,
wherein the stimulation timing control device is further configured to calculate the generating timings to cause the feature points appear at the same time based on the plurality of latencies respectively calculated for the plurality of stimulating units, and a trigger signal generator configured to generate a trigger signal based on the calculated generating timings calculated, and
wherein the plurality of stimulating units generates the stimuli in response to the trigger signal.

10. The biometric information measuring system as claimed in claim 9,
wherein the trigger signal generator generates a plurality of said trigger signals respectively output to the plurality of stimulating units, and
wherein the plurality of stimulating units respectively generates the stimulus in response to the plurality of trigger signals.

11. The biometric information measuring system as claimed in claim 10,
wherein the nerve stimulating apparatus includes a plurality of sub-stimulators respectively including the plurality of stimulating units, and wherein the trigger signal generator generates the plurality of trigger signals respectively output to the plurality of stimulating units of the plurality of sub-stimulators.

12. The biometric information measuring system as claimed in claim 6,
wherein the magnetic field is generated by the living body, and
wherein the stimuli applied by the plurality of stimulating units to the living body are electrical stimuli.

13. The biometric information measuring system as claimed in claim 12, further comprising an electric potential measuring device that is configured to measure an electric potential difference at the particular nerve region of the living body, in addition to the biomagnetic field measuring device.

14. A method of setting stimulus generating timings of a biometric information measuring system including a nerve stimulating apparatus including a plurality of stimulating units configured to respectively apply stimuli to a plurality of nerve regions branching from a particular nerve region of a living body, the stimuli being electrical stimuli, magnetic stimuli, acoustic stimuli, or mechanical stimuli, a biomagnetic field measuring device configured to measure response results of the particular nerve region as biometric information, the response results being obtained in response to the stimuli respectively applied to the plurality of nerve regions, and a stimulation timing control device configured to set generating timings of respectively generating the stimuli at the plurality of stimulating units, the method comprising:
generating the stimuli at the multiple stimulating units respectively based on the generating timings set by the stimulation timing control device; and
setting the generating timings of generating the stimuli at the plurality of stimulating units based on the response results of the particular nerve region, the response results being obtained in response to the stimuli that are respectively generated at the plurality of stimulating units and that are respectively applied to the plurality of nerve regions, and each of the response results being a magnetic field measured by the biomagnetic field measuring device,
wherein the setting of the generating timings includes respectively calculating a plurality of latencies each indicating a duration from when a respective one of the stimuli is applied to the living body to when a corresponding one of feature points appears in a response of the living body, for the plurality of stimulating units, based on current data estimated based on the measured magnetic field, and setting the generating timings based on the plurality of calculated latencies.

* * * * *